United States Patent
Richter et al.

(10) Patent No.: US 9,820,998 B2
(45) Date of Patent: Nov. 21, 2017

(54) USE OF BISPHOSPHONATES AS HIV/AIDS ADJUNCTIVE TREATMENT

(71) Applicants: BIOREST LTD., Tel Aviv (IL); OREGON HEALTH & SCIENCE UNIVERSITY, Portland, OR (US)

(72) Inventors: Yoram Richter, Ramat Hasharon (IL); Gershon Golomb, Efrat (IL); Jonah B. Sacha, Beaverton, OR (US)

(73) Assignees: BIOREST LTD., Tel Aviv (IL); OREGON HEALTH & SCIENCE UNIVERSITY, Portland, OR (US)

( * ) Notice: Subject to any disclaimer, the term of this patent is extended or adjusted under 35 U.S.C. 154(b) by 42 days.

(21) Appl. No.: 14/713,050

(22) Filed: May 15, 2015

(65) Prior Publication Data

US 2015/0328237 A1 Nov. 19, 2015

Related U.S. Application Data

(60) Provisional application No. 61/994,560, filed on May 16, 2014.

(51) Int. Cl.
A61K 31/663 (2006.01)
A61K 31/675 (2006.01)
(Continued)

(52) U.S. Cl.
CPC .......... *A61K 31/663* (2013.01); *A61K 9/0019* (2013.01); *A61K 9/127* (2013.01);
(Continued)

(58) Field of Classification Search
CPC ................................................... A61K 31/663
See application file for complete search history.

(56) References Cited

U.S. PATENT DOCUMENTS

2005/0113331 A1* 5/2005 Prniak ................... A61K 31/66
514/49
2006/0079487 A1 4/2006 Sanders et al.
(Continued)

FOREIGN PATENT DOCUMENTS

| WO | WO 2005/002545 | 1/2005 |
| WO | WO 2005/023270 | 3/2005 |
| WO | WO 2012/054807 | 4/2012 |

OTHER PUBLICATIONS

International Search Report and Written Opinion for corresponding application No. PCT/US2015/030952 dated Jul. 31, 2015, 12 pages.
(Continued)

*Primary Examiner* — Benjamin Packard
(74) *Attorney, Agent, or Firm* — Cadwalader, Wickersham & Taft LLP

(57) ABSTRACT

The present invention relates to use of bisphosphonate formulations for the treatment and management of HIV/AIDS. The method of the invention comprises administering a formulation comprising an effective amount of a bisphosphonate that specifically inhibits the activity and/or decreases the number of monocytes and/or macrophages, thereby reducing or eliminating HIV reservoirs. The invention also provides a method of complementing an HIV antiviral therapy, such as the highly active antiretroviral therapy (HAART), with a bisphosphonate formulation to improve clinical outcome.

19 Claims, 8 Drawing Sheets

(51) Int. Cl.
*A61K 45/06* (2006.01)
*A61K 9/00* (2006.01)
*A61K 9/127* (2006.01)
*A61K 47/24* (2006.01)
*A61K 9/51* (2006.01)

(52) U.S. Cl.
CPC ............ *A61K 31/675* (2013.01); *A61K 45/06* (2013.01); *A61K 47/24* (2013.01); *A61K 9/5153* (2013.01)

(56) References Cited

U.S. PATENT DOCUMENTS

| | | | |
|---|---|---|---|
| 2006/0210639 A1* | 9/2006 | Liversidge | A61K 9/0019 424/489 |
| 2008/0255070 A1 | 10/2008 | Oldfield et al. | |
| 2010/0015213 A1* | 1/2010 | Golomb | A61K 9/127 424/450 |

OTHER PUBLICATIONS

Serafini et al., "Effect of Macrophage Depletion on Viral DNA Rebound Following Antiretroviral Therapy in a Murine Model of AIDS (MAIDS)," Antiviral Research, Elsevier BV, NL, vol. 81, No. 2, dated Feb. 1, 2009, pp. 93-102.

* cited by examiner

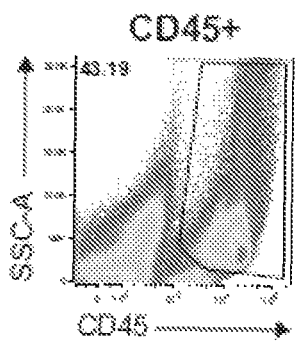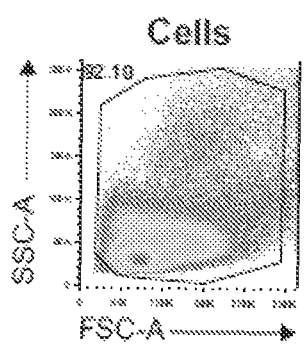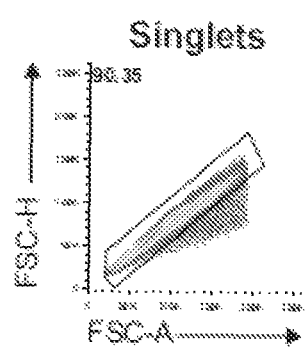
FIG. 5A  FIG. 5B  FIG. 5C
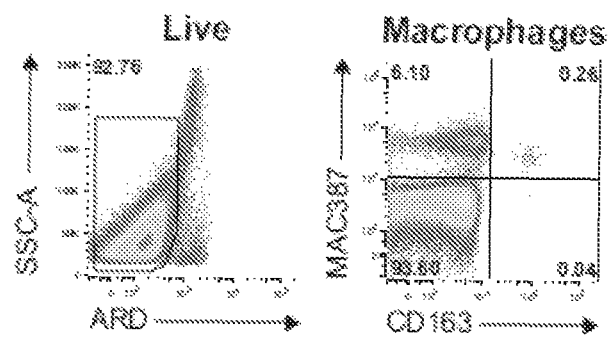
FIG. 5D  FIG. 5E

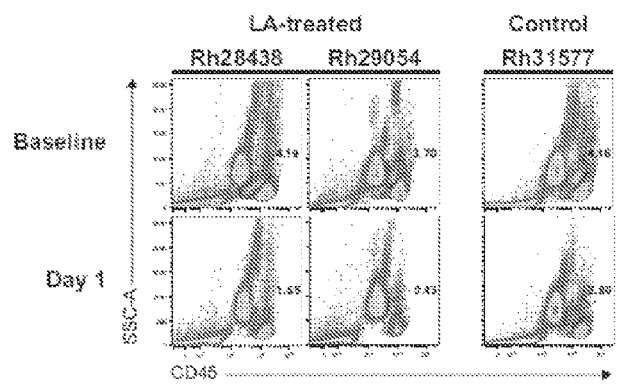
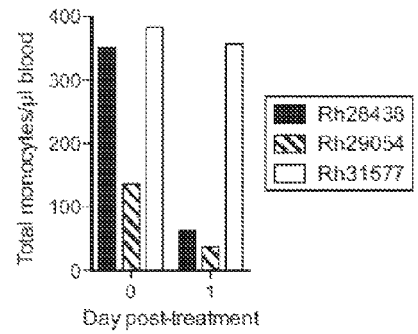
FIG. 8A
FIG. 8B
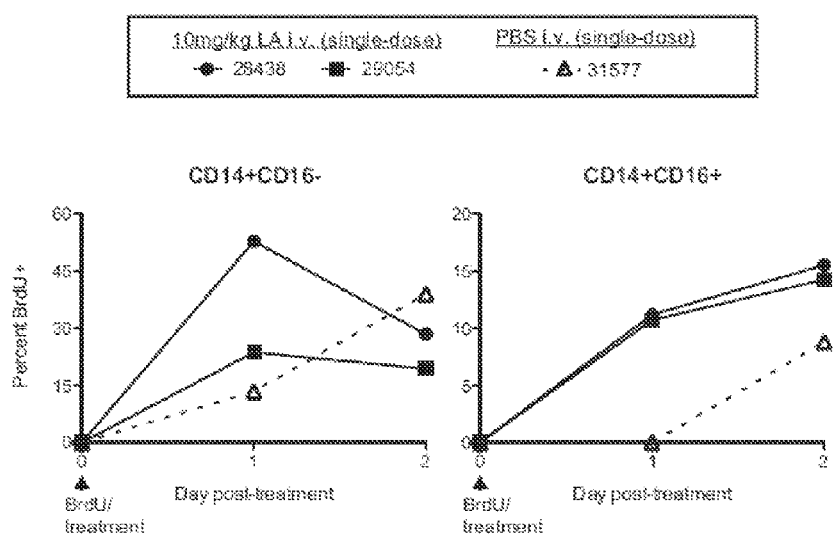
FIG. 8C

USE OF BISPHOSPHONATES AS HIV/AIDS ADJUNCTIVE TREATMENT

FIELD OF THE INVENTION

The present invention relates to use of compositions designed for the treatment or management of HIV/AIDS. The method of the invention comprises administering a formulation comprising an effective amount of a bisphosphonate to inhibit monocyte and/or macrophage activity and/or to reduce inflammation and/or to decrease HIV reservoirs. Use of the compositions may complement antiviral therapy, such as the highly active antiretroviral therapy (HAART).

BACKGROUND OF THE INVENTION

Human immunodeficiency virus infection/acquired immunodeficiency syndrome (HIV/AIDS) is a disease of the human immune system caused by the infection with human immunodeficiency virus (HIV). Since its discovery in the early 1980s, AIDS has become a pandemic and caused more than 25 million deaths. Approximately 35 million people are currently living with HIV/AIDS globally, urgently in need of effective, affordable, long-term treatment and management of the disease.

HIV can infect a variety of immune cells, with $CD4^+$ T cells and monocytes/macrophages being the major targets. HIV attacks a target cell first by fusion of the viral envelope with the cell membrane and release of the HIV capsid into the cell. Inside the infected cell, the single-stranded RNA genome of the HIV is reverse transcribed into a double-stranded viral DNA, and the viral DNA is integrated into the infected cell's genome. Then cellular machineries of the infected cell are hijacked to produce the RNA genome as well as the protein components of the virus, which assemble into immature HIV virions inside the infected cell. After the final assembly at the cell surface, the immature HIV-virions bud from the cell membrane of the infected cell and after the final step of protease cleavage, the resultant mature virions are released, completing a replication cycle. HIV rapidly replicates in the first 2-4 weeks after infection, leading to a marked drop in the number of circulating $CD4^+$ T cells. Upon mobilization of the still largely intact immune system to fight HIV replication, the virus level is controlled and the $CD4^+$ T cell counts stabilize such that the HIV infection enters clinical latency, and the latency can last from about three years to over 20 years. As the HIV erodes the immune system, eventually the level of $CD4^+$ T cells drops to an alarming level and HIV infection progresses into AIDS. AIDS patients often die of opportunistic infections as a result of the collapse of their immune systems. HIV may also damage the nervous system, entering the brain through infected immune cells early on in the infection and further spreading to the central nervous system (CNS)-resident immune cells, such as microglia and astrocytes. These infections may damage the brain and spinal cord and cause symptoms such as confusion and forgetfulness, behavioral changes, headaches, progressive weakness, and loss of sensation in the arms and legs.

The mainstream treatment of AIV/AIDS is the highly active antiretroviral therapy (HAART), which uses combinations (or "cocktails") of compounds that include multiple classes of antiviral agents. Virus production in infected individuals is largely the result of a dynamic process involving continuous rounds of de novo infection of and replication in activated $CD4^+$ T cells with rapid turnover of both free virus and virus-producing cells. These antiviral cocktails inhibit steps of HIV's replication cycle, including entry, reverse transcription, integration, assembly and release. HAART therefore suspends the HIV replication cycle, causing depletion of the immature HIV virions and the host cells, resulting in containment of HIV infection.

Current antiviral therapy, however, does not eradicate HIV infection, because other HIV-infected cells, including the resting memory $CD4^+$ T cells and the monocytes/macrophages, have long half-lives and therefore serve as virus reservoirs. HAART also suffers the drawbacks of high cost, adverse toxic effects, drug interactions, and drug resistance. These adverse effects sometimes make it necessary to introduce structured therapy interruptions ("TI", or drug holidays) or cease the treatment altogether. Drug resistance is a significant problem in HAART: the reverse transcription of HIV RNA is prone to mistakes, resulting in introduction of mutations into the viral genome. Continued antiviral drug administration provides natural selection for drug-resistant mutant virus strains. There is a theory that TI may allow more "fit" wild-type drug-susceptible viruses to outgrow the less "fit" drug-resistant mutant strains. For this additional reason, it is often recommended to interrupt the antiviral therapy in a structured manner. However, rebound of plasma viral loads (VL) and decline in $CD4^+$ T cell counts is common during TI, thereby negating the effect of the HAART treatment. Virions, in particular drug-resistant virions, sequestered in HIV reservoirs are no longer suppressed during TI and may mature and be released. This is thought to be the cause of therapy setback during TI and the less effective suppression frequently afforded by HAART when subsequently reintroduced.

Infected resting memory $CD4^+$ T cells, monocytes and macrophages are reservoirs for HIV, including the drug-resistant strains. In addition, monocytes produce cytokines, e.g., TNFα, that induce HIV replication in other infected cells, e.g., $CD4^+$ T cells. Infected activated macrophages are able to trigger apoptosis of uninfected T cells and protect HIV-infected T cells from apoptosis. Monocytes and macrophages therefore provide a pool of viruses ready to replicate during TI, and their physiological activity further amplifies the damage of HIV infection to the immune system. A few studies have targeted monocytes and macrophages as a treatment of HIV/AIDS, however, the therapeutic efficacy of these approaches has been limited.

Clinical studies testing the effect of purging circulating monocytes by selective apheresis produced mixed results. Selective apheresis involves passing the blood of HIV-infected, HAART-receiving patients through an extracorporeal apparatus to remove circulating monocytes and granulocytes. In one study, apheresis during HAART treatment did not affect plasma HIV-1 RNA load compared to controls, but reduced TNFα level and increased $CD4^+$ T cell counts after 3-4 apheresis sessions. (Beretta, A. et al., J. Biol. Regulators and Homeostatic Agents 14, 27-31 (2000).) In another study, selective apheresis of monocytes and granulocytes was conducted during the first 5 weeks of TI. Upon reintroduction of HAART, the apheresis group exhibited an increase in $CD4^+$ T cell counts. HAART reintroduction failed to suppress viral rebound in most, but not all, of the control group, whereas, the most of the apheresis group exhibited virologic suppression. A reduction of monocyte HIV viral load of up to 52% was observed in some of the apheresis group, but enhancement comparable to controls was observed in others. (Hasson, H. et al., J. Med. Virol. 79, 1640-49 (2007).) These limited results might be accounted for by the fact that apheresis results in an average reduction of only 30% of circulating monocytes, and circulating monocytes represent a small fraction of the total body monocyte/macrophage pool. Another limitation of such approaches is that apheresis is an invasive and time-consuming in-patient procedure, which can significantly burden patients.

Other researchers also tested macrophage-inhibiting drugs in HIV animal models and saw positive effects on viral load control and CD4$^+$ T cell rebound after HAART cessation. To achieve the specific and effective targeting of macrophages, the drugs were loaded in erythrocyte ghosts (erupted red blood cells). (see Cervasi, B. et al., J. Viol. 80, 10335-45 (2006); Serafini, S. et al., Antirivial Res. 81, 93-102 (2009).) Erythrocyte ghosts are difficult to prepare and store, however, making them a less than ideal choice for delivering drugs in great demand. Additionally, erythrocyte ghosts release their contents rapidly because of inherent leakage and the normal physiological process that eliminates red blood cells. The resultant elevated plasma drug concentration leads to toxicological problems. (See Lanao, J. M. et al., J. Drug Targeting 15(1), 21-36 (2007).)

Because a reliable cure or effective HIV vaccine still evades scientists, it is vital to slow the progression of HIV infection and maintain clinical latency as long as possible. Accordingly, there is a need in the art for a safe and effective approach to suppress virus replication in HIV/AIDS patients to complement HAART, in particular during TI. In addition, it is desirable that such approach is easy to administer and has the potential for mass production to meet the demand of a large HIV/AIDS population.

The current invention provides the advantage of specifically targeting monocytes and macrophages, the HIV latent reservoirs, preventing or delaying the rebound of HIV viral loads. The formula is expected to improve TI safety and extend the length of TI. Considering the physical and financial burden of HAART on HIV/AIDS patients and the public health system, safer and longer TI is highly desirable for the long-term management of the disease. Compared to the prior art, as adjunct therapy to HIV/AIDS antiviral treatment, the formulation of the invention is easy to administer, non-invasive, easy to store and distribute, and adaptable for mass production.

SUMMARY OF THE INVENTION

The present invention relates to use of medicament compositions for the treatment or management of HIV/AIDS, particularly, to complement and maintain the effect of antiviral therapy during TI or after cessation of an antiviral therapy. The methods of the invention comprise the administration of an effective amount of one or more therapeutic agents in a formulation designed to inhibit the activity of and/or diminish the number of phagocytic cells. Such phagocytic cells include, but are not limited to, macrophages and monocytes. The therapeutic agents preferably include a bisphosphonate. Such administration according to the invention aims at suppressing or depleting the HIV reservoirs (including latent reservoirs) during antiviral therapies and TI as well as helping increase the level of peripheral CD4$^+$ T cells, so as to prevent or delay the rebound of viruses, in particular when TI is indicated.

In particular, the present invention relates to a method of depleting the number of HIV reservoirs (i.e., monocytes/macrophages) and/or inhibiting their function, for treating or managing HIV/AIDS, by administering to an individual in need thereof an effective amount of a formulation comprising a bisphosphonate, optionally in combination with other therapeutic agents.

Bisphosphonates (formerly called diphosphonates) are compounds characterized by two carbon-phosphate (C—P) bonds. They are analogs of the endogenous inorganic pyrophosphate which is involved in the regulation of bone formation and resorption. If the two bonds are located on the same carbon atom (P—C—P) they are termed geminal bisphosphonates, and the term bisphosphonates is generally used for geminal and non-geminal bisphosphonates. The bisphosphonates and pyrophosphates may at times together form polymeric chains. In the clinical setting, bisphosphonates are mainly used as potent inhibitors of bone resorption and ectopic calcification; more recently, their clinical indications in other areas are being explored and liposome-encapsulated bisphosphonates have been shown to treat cardiovascular conditions, including restenosis. See, e.g., U.S. Pat. No. 6,719,998.

The formulation used in the method may comprise an encapsulated, an embedded, or a particulate bisphosphonate. The formulations comprise particles having properties that permit the formulation to enter a cell primarily or exclusively via phagocytosis and therefore the formulation is expected to specifically target phagocytic cells. Without being bound by theory, once phagocytosed by the targeted phagocytic cells, macrophages and monocytes, the bisphosphonate is released into the phagocytic cells, and inhibits their function and/or depletes their number.

In one embodiment, the formulation used in the method comprises a bisphosphonate encapsulated in liposomes of an appropriate dimension. The liposome-encapsulated bisphosphonate specifically targets monocytes and/or macrophages by virtue of its properties, such as size, charge, conductivity and the lipid composition of the liposomes, which allow the formulation to be taken up primarily or exclusively by phagocytosis. Once taken up by the phagocytic cell, the liposome-encapsulated bisphosphonate is released inside the cell to inhibit the activity of and/or kill the monocytes and/or macrophages.

In another embodiment, the method uses a formulation comprising a bisphosphonate embedded in a carrier having a particle size appropriate for phagocytic uptake. The embedding carrier may also have a charge or surface property that renders it a phagocytic target of macrophages and/or monocytes.

In yet another embodiment, the method uses a formulation comprising a bisphosphonate in particulate form, the particulate having a size appropriate for phagocytic uptake.

In one embodiment, the formulation is administered during an antiviral therapy. In another embodiment, the formulation is administered during TI. In yet another embodiment, the formulation is administered both during an antiviral therapy and during TI. In still another embodiment, the formulation is administered just before cessation of antiviral therapy. The antiviral therapy may be HAART.

Advantages of the invention include specific targeting of monocytes and macrophages, the HIV reservoirs, and preventing or delaying the rebound of HIV viral loads. The formula is expected to improve TI safety and extend the TI period. Considering the physical and financial burden of HAART on both HIV/AIDS patients and the public health system, safer and longer TI is highly desirable for the long-term management of the disease. Compared to the prior art, as adjunct therapy to HIV/AIDS antiviral treatment, the formulation of the invention is easy to administer, non-invasive, easy to store and distribute, and adaptable for mass production.

BRIEF DESCRIPTION OF THE DRAWINGS

FIG. 1A illustrates the absolute frequency of monocytes; FIG. 1B illustrates the relative frequency of monocytes.

FIG. 2A shows concentrations of serum albumin; FIG. 2B shows concentration of alanine transaminase; FIG. 2C shows concentrations of alkaline phosphatase; FIG. 2D shows total bilirubin.

FIG. 4A: whole blood; FIG. 4B: $CD14^+CD16^-$; FIG. 4C: $CD14^+CD16^+$; FIG. 4D: $CD14^-CD16^+$.

FIGS. 5A-5E illustrate a gating strategy for the identification of macrophages in tissues and bone marrow.

FIG. 7A: bone marrow; FIG. 7B: liver; FIG. 7C: colon.

FIGS. 8A-8C illustrate the effect of liposomal alendronate treatment on monocytes in non-human primate model. FIG. 8A shows monocyte frequency in whole blood assessed by CD45 staining versus side scatter profile; FIG. 8B shows absolute monocyte counts; FIG. 8C shows monocyte turnover following using BrdU.

Figures 1A, 1B:
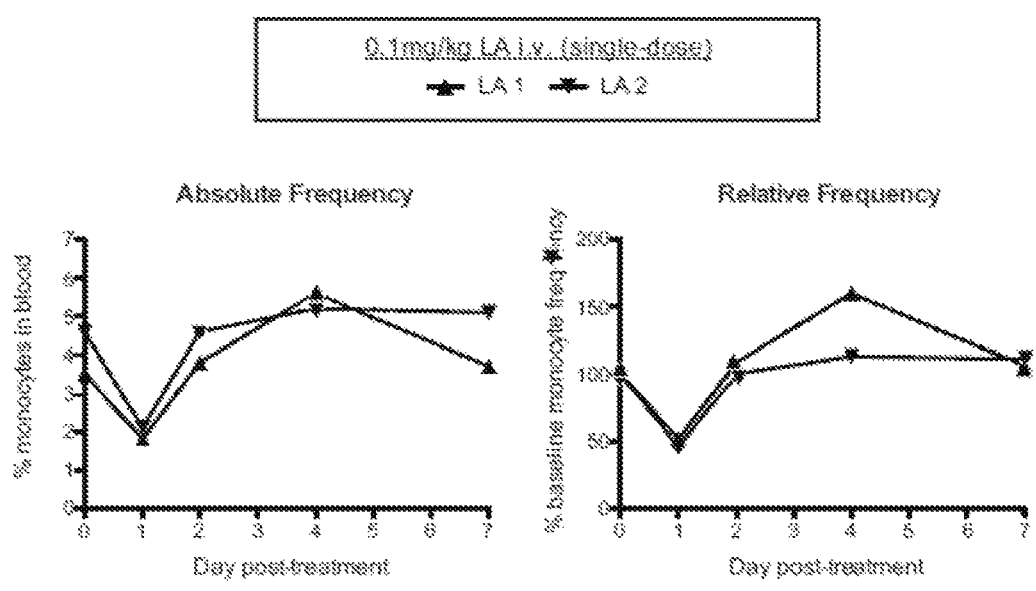
FIGS. 1A-1B illustrate the effect of administering to cynomolgus macaques a single dose of 0.1 mg/kg liposomal alendronate, compared to vehicle control, on peripheral CD4+ counts over 7 days.

Note that the drawings are provided as an exemplary understanding of the present invention and to schematically illustrate particular embodiments of the present invention. The skilled artisan will readily recognize other similar examples equally within the scope of the invention. The drawings are not intended to limit the scope of the present invention as defined in the appended claims.

DETAILED DESCRIPTION OF THE INVENTION

Monocytes and macrophages are susceptible to HIV infection, and the infected monocytes and macrophages have the viral DNA integrated into their genomes. Because monocytes and macrophages have long lives and do not cycle frequently, they act as reservoirs of HIV during antiviral therapy, harboring immature HIV virions, which can be released upon interruption of antiviral therapy. Monocytes and macrophages also secrete a variety of chemokines that promote the further spread of HIV infection.

The present invention provides a medicament formulation for use in treating HIV infection by decreasing or inhibiting monocyte/macrophage activity and/or eliminating or diminishing the quantity of monocytes/macrophages for a period during and/or following an antiviral therapy. The method of the invention comprises administering an effective amount of a bisphosphonate in a formulation that is selectively taken up by monocytes and/or macrophages. The administration is contemplated to complement antiviral therapy, such as HAART, to prevent or delay the rebound of viral loads and increase $CD4^+$ T cells counts during an interruption of antiviral therapy. It is expected this may allow the TI period to be extended, thereby delaying the need to reintroduce antiviral therapy.

In one embodiment, the formulation is administered during an antiviral therapy to initiate the monocyte/macrophage inhibiting effect that lasts until cessation of the therapy and during TI. It is desired that the HIV-inhibiting effect of the formulation lasts during TI, and therefore the formulation may be administered within a short period before an interruption of an antiviral therapy, for example, about 3 days, or about 5 days, or about 7 days, or about 10 days before an antiviral therapy is interrupted. In another embodiment, the formulation is administered during TI. In yet another embodiment, the formulation is administered both during an antiviral therapy and during TI. Multiple administrations of the formulation during an antiviral therapy and/or during TI to reach the effective amount and to maintain the HIV-inhibiting effect for a desired period of time are within the scope of the invention.

Use of the formulation of the present invention, e.g., the encapsulated, embedded or particulate bisphosphonate, selectively inactivates and/or depletes the number of monocytes and/or macrophages, which are important HIV reservoirs. Because of its particular size and/or other physiochemical properties, the formulation will enter cells primarily or exclusively by phagocytosis. Thus, the formulation of the invention specifically targets phagocytes such as monocytes and macrophages. Once inside the phagocytic cells, the bisphosphonate is released and inhibits, inactivates, disables, kills and/or depletes the monocytes and/or macrophages.

The term "phagocytosis" as used herein refers to a preferred means of entry into a phagocytic cell and is well understood in the art. However, the term should be understood to also encompass other forms of endocytosis which may also accomplish the same effect. In particular, it is understood that pinocytosis, receptor-mediated endocytosis and other cellular means for absorbing/internalizing material from outside the cell are also encompassed by the methods and compositions of the present invention.

Bisphosphonates

The therapeutic agent used in the formulation is a bisphosphonate or analog thereof. The term bisphosphonate as used herein denotes both germinal and non-germinal bisphosphonates. The therapeutic agent also encompasses in its scope polymeric chains of bisphosphonates or pyrophosphate, particularly such chains consisting of up to 40 bisphosphonate monomers. In one embodiment, the bisphosphonate has the following formula (I):

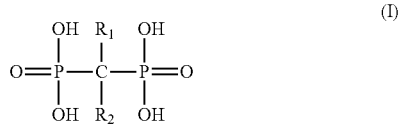

wherein $R_1$ is H, OH, or a halogen atom; and $R_2$ is halogen; linear or branched $C_1$-$C_{10}$ alkyl or $C_2$-$C_{10}$ alkenyl optionally substituted by heteroaryl or heterocyclyl $C_1$-$C_{10}$ alkylamino or $C_3$-$C_8$ cycloalkylamino where the amino may be a primary, secondary or tertiary; —NHY where Y is hydrogen, $C_3$-$C_8$ cycloalkyl, aryl or heteroaryl; or $R_2$ is —SZ where Z is chlorosubstituted phenyl or pyridinyl.

Other bisphosphonates that can be used in accordance with the invention include, but are not limited to, clodronate, tiludronate, 3-(N,N-dimethylamino)-1-hydroxypropane-1,1-diphosphonic acid, i.e., dimethyl-APD; 1-hydroxy-ethyl-idene-1,1-bisphosphonic acid, i.e., etidronate; 1-hydroxy-3 (methylpentylamino)-propylidene-bisphosphonic acid, (ibandronic acid), i.e., ibandronate; 6-amino-1-hydroxy-hexane-1,1-diphosphonic acid, i.e., amino-hexyl-BP; 3-(N-methyl-N-pentylamino)-1-hydrox-ypropane-1,1-diphosphonic acid, i.e., methyl-pentyl-APD; 1-hydroxy-2-(imidazol-1-yl)ethane-1,1-diphosphonic acid, i.e., zoledronic acid; 1-hydroxy-2-(3-pyridyl)ethane-1,1-diphosphonic acid (risedronic acid), i.e., risedronate; 3-[N-(2-phenylthioethyl)-N-methylamino]-1-hydroxypropane-1,1-bisphosphonic acid; 1-hydroxy-3-(pyrrolidin-1-yl)propane-1,1-bisphosphonic acid, 1-(N-phenylaminothiocarbonyl)methane-1,1-diphosphonic acid, i.e., FR 78844 (Fujisawa); 5-benzoyl-3,4-dihydro-2H-pyra-zole-3,3-diphosphonic acid tetraethyl ester, i.e., U81581 (Upjohn); and 1-hydroxy-2-(imidazo[1,2-a]pyridin-3-yl)e-thane-1,1-diphosphonic acid, i.e., YM 529, or analogs thereof. Formula of some of the above bisphosphonates are described in U.S. Pat. No. 6,719,998, which is herein incorporated by reference.

In a specific embodiment, the bisphosphonate is alendronate or an analog thereof. In such an embodiment, formula I has R1=OH and R2=$(CH_2)_3$—$NH_3$.

Alendronate is a second-generation nitrogenous bisphosphonate that provides a good therapeutic window [17, 21, 22]. In general, nitrogenous bisphosphonates comprise a preferred subclass of bisphosphonates particularly useful in the invention. Such bisphosphonates may be selected on the basis of their ability to mimic the biological activity of alendronate. This includes, for example: in vitro activity in inhibiting activity of phagocytic cells, e.g. macrophages and fibroblasts once inside such cell; inhibition of secretion of IL-1 and/or IL-6 and/or TNF-α from macrophages; and in vivo activity, e.g., the ability of the tested formulations to deplete or disable blood monocytes in an animal model or in humans or to treat HIV/AIDS.

Formulation, Pharmaceutical Composition and Route of Administration

The formulation of the invention may be prepared to have a particle size appropriate for cell internalization only or primarily by phagocytosis, thus imparting specificity to phagocytic cells, such as macrophages and monocytes. The formulation containing a bisphosphonate according to the invention is preferably prepared such that the formulation has a particle size that will only or primarily be internalized by phagocytosis, that is, preferably larger than 0.03 microns. For example, such formulation may have a particle diameter, for example an average diameter, of between about 0.03-1.0 microns, or between about 0.1-0.3 microns, or between about 0.1-0.18 microns, or between about 0.07-0.5 microns, or between about 0.07-0.15 microns. Any method known in the art can be used to determine the size of the formulation particles before administration to a patient in need thereof. For example, a Nicomp Submicron Particle Sizer (model 370, Nicomp, Santa Barbara, Calif.) utilizing laser light scattering can be used.

Any method known in the art can be used to incorporate a bisphosphonate into a formulation that can only or primarily be taken up into cells via phagocytosis. The formulation may sequester the bisphosphonate for a sufficient time to enhance delivery to the target site. The formulation may have a charge or surface property that effects or enhances phagocytosis. Further, the formulation may discharge the bisphosphonate when within the target cells (e.g., monocytes and/or macrophages) at the target site.

In one embodiment, the bisphosphonate is encapsulated. Encapsulated forms are intended to mean enclosures having a structure that serves as a barrier to the therapeutic agent, such as for example polymeric or lipoid delivery systems. In one embodiment, the encapsulating agent is a liposome. The liposome comprises lipid ingredients that encapsulate the bisphosphonate and may be a single lipid layer or may be multi-lamellar. The liposomes may be positively charged, neutral or negatively charged. In a preferred embodiment, the liposomes are negatively charged. Suitable liposomes in accordance with the invention are preferably non-toxic liposomes such as, for example, those prepared from phosphatidyl-choline, phosphoglycerol, and cholesterol. In one embodiment, the lipid ingredients may comprise, for example, diastearoylphosphatidylcholine (DSPC), diastearoylphosphatidylglycerol (DSPG) and cholesterol (chol). For example, the liposome may comprise DSPC:DSPG:chol in a 3:1:2 molar ratio. The ratio of the mass of the bisphosphonate to that of the lipid ingredient, called the drug:lipid ratio, may be about 1:5 to 1:8 by weight, or about 1:6 to 1:7 by weight. In certain embodiments, such as, e.g., sodium alendronate encapsulated in DSPC, DSPG and cholesterol, a 1:5.7 drug:lipid mass ratio—equal to approximately a 1:3 molar ratio for sodium alendronate—may be used. As another example, encapsulation of clodronate disodium in the same lipid ingredient, a mass ratio of approximately 1:5.4 may be used, which is equivalent to a 1:3 molar ratio. Determination of the molar ratio for other bisphosphonates and other lipid combinations is within the skill in the art.

The liposomes of the formulation have specific characteristics, including size, charge, pH, conductivity and osmolality that allow uptake primarily via phagocytosis. The diameter of the liposomes used may be in a size range suitable for phagocytosis by monocytes or macrophages, for example, a range of 0.03-1.0 microns or the diameter may have a size or size range within that range, as described herein. For example, in one embodiment, the liposomes may have a diameter of about 0.08±0.005 microns. The conductivity of the liposome may be, for example, between about 13.5-17.5 ms/cm. The external osmolality of the liposome may be matched with that of the human body and the internal osmolality may be lower, as a lower osmolality may enhance stability of the formulation. Thus, for example the internal osmolality may be between about 340-440 mO/kg. The internal pH of the liposome and/or the liposome formulation may be about 6.9.

Liposomes may be prepared by any of the methods known in the art (see, e.g., Mönkkönen, J., et al., J. DRUG TARGET, 2:299-308 (1994); Mönkkönen, J., et al., CALCIF. TISSUE INT., 53:139-145 (1993); Lasic, D., LIPOSOMES TECHNOLOGY INC., Elsevier, Chapter 3, pp. 63-105 (1993); Winterhalter, M, Lasic, D. D., CHEM. PHYS. LIPIDS, 54(1-3):35-43 (September 1993); Epstein-Barash, H., et al., J. CONTROLLED RELEASE, 146:182-195 (2010); Epstein, H. et al., AAPS J, 10:505-515 (2008); U.S. Pat. No. 7,008,645; U.S. Patent Publication No. 2010/0015213; U.S. Patent Publication No. 2004/0266734; U.S. patent application Ser. No. 13/804,707); all of which are incorporated herein by reference in their entireties). In one such method, liposomes are formed into stacks of liquid crystalline bilayers that are hydrated into hydrated lipid sheets, which detach during agitation and self-close to form large, multilamellar vesicles (MLV) known as thin lipid film hydration technique. Once these particles are formed, the size of the particles may be reduced using sonic energy (sonication) or mechanical energy (extrusion). Sonication typically produces small, unilamellar vesicles (SUV); lipid extrusion, which forces a lipid suspension through a series of poly carbonate filter—typically 0.8, 0.4, 0.2 and 0.1 micron membranes—at high pressure (up to 500 psi), produces particles having a diameter near the pore size of the filter used.

Substantially uniform liposomes may be prepared by a low pressure method, as described in U.S. Patent Publication No. 2004/0266734 and co-pending U.S. patent application Ser. No. 13/804,707, both of which are incorporated by reference herein. Briefly, for example, the therapeutic agent may be mixed with preselected lipids to form vesicles, the vesicles may be extruded in a single-stage through a filter having a single pre-selected size, followed by ultrafiltration. This method can produce liposomes having a particle size of between about 0.03-0.5 microns, between about 0.07-0.12 microns, between about 0.07-0.15 microns, between about 0.1-0.18 microns, and between about 0.1-0.3 microns.

In one embodiment, the liposomes may be prepared as follows: (1) mixing bisphosphonate and preselected lipids to form multi-lamellar vesicles (MLV), (2) producing vesicles of the final size, and (3) purification and selection for the bisphosphonate-loaded liposomes. In step (1), the bisphosphonate is typically resolved in water, while the accurately weighed lipid ingredients are dissolved in a solvent, such as chloroform:methanol (9:1), ethanol:t-butanol (1:1), or ethanol:t-butanol:water (77:77:6 v/v/v). The bisphosphonate solution is then mixed into the lipids solution, and mild heating may be employed to aid in the mixing. This process results in efficient encapsulation of the bisphosphonate into MLV that are not homogeneous in size and larger than the desired final size. In step (2), a mechanical method is used to reduce the size of the vesicles and render the vesicles into a uniform size and shape. Methods known in the art include sonication and extrusion. The liposomes may be extruded by applying pressure and forcing the lipid-drug mixture through a series of filters with decreasing pore sizes. Alternatively, the liposomes may be extruded by the method described in co-pending U.S. patent application Ser. No. 13/804,707 using a single-stage filtration and a single pore-size filter under low pressure. This method may save operating costs and time and may increase yield over multi-staged, high pressure extrusions. In step (3), the properly encapsulated bisphosphonate is separated from unencapsulated bisphosphonate, solvents and lipids. Exemplary methods for this step include gel filtration through a gel column and ultrafiltration through a membrane.

In another embodiment, the bisphosphonate is embedded in a carrier, i.e., in an embedding agent having desired properties, for example, having particle diameter in the range of 0.03-1.0 microns. The bisphosphonate that is embedded includes bisphosphonates that are embedded, enclosed, and/or adsorbed within the carrier, dispersed in the carrier matrix, adsorbed or linked on the carrier surface, or a combination of any of these forms. In specific embodiments, the embedding agent (or carrier) is a microparticle, nanoparticle, nanosphere, microsphere, microcapsule, or nanocapsule (see e.g., M. Donbrow in: Microencapsulation and Nanoparticles in Medicine and Pharmacy, CRC Press, Boca Raton, Fla., 347, 1991). The term "carrier" includes both polymeric and non-polymeric preparations. In a specific embodiment, the embedding agent is a nanoparticle. The nanoparticles can be spherical, non-spherical, or polymeric particles. The therapeutic agent may be embedded in the nanoparticle, dispersed uniformly or non-uniformly in the polymer matrix, adsorbed on the surface, or in combination of any of these forms. In a preferred embodiment, the polymer used for fabricating nanoparticles is biocompatible and biodegradable, such as poly(DL-lactide-co-glycolide) polymer (PLGA). However, additional polymers which may be used for fabricating the nanoparticles include, but are not limited to, PLA (polylactic acid), and their copolymers, polyanhydrides, polyalkyl-cyanoacrylates (such as polyisobutylcyanoacrylate), polyethyleneglycols, polyethyleneoxides and their derivatives, chitosan, albumin, gelatin and the like. The embedded bisphosphonate may have a particle diameter in the size range of, for example, 0.03-1.0 microns, or the particle diameter may have a size or size range within that range, as described herein, suitable for phagocytosis by monocytes or macrophages, for example an average diameter of between about 0.03-1.0 microns, or between about 0.1-0.3 microns, or between about 0.1-0.18 microns, or between about 0.07-0.5 microns, or between about 0.07-0.15 microns.

In another embodiment, the bisphosphonate is in particulate form, the particles each being of desired properties. A particulate form includes any insoluble suspended or dispersed particulate form which is not encapsulated or embedded. A bisphosphonate which is in particulate form may be in the form of suspended or dispersed colloids, aggregates, flocculates, insoluble salts, insoluble complexes, and polymeric chains. Such particulates are insoluble in the fluid in which they are stored/administered (e.g., saline or water) as well as the fluid in which they provide their therapeutic effect (e.g., blood or serum). Typically, "insoluble" refers to a solubility of one (1) part of a particulate compound in more than ten-thousand (10,000) parts of a solvent. Any method known in the art to make particulates or aggregates can be used. The particulate bisphosphonate may have a particle diameter in the size range of, for example, 0.03-1.0 microns, or the particle diameter may have a size or size range within that range, as described herein, suitable for phagocytosis by monocytes or macrophages, for example an average diameter of between about 0.03-1.0 microns, or between about 0.1-0.3 microns, or between about 0.1-0.18 microns, or between about 0.07-0.5 microns, or between about 0.07-0.15 microns.

While each of the formulations of the invention is designed as a target for phagocytosis, phagocytic cells other than monocytes and macrophages, such as for example neutrophils, may engulf the particle but will either be unaffected or less affected, because the activity of the bisphosphonates is relatively exclusive to monocytes and macrophages. Non-phagocytic cells are relatively incapable of taking up the formulation due to the particular physio-chemical properties of the liposomal formulation.

After being taken-up by the monocytes/macrophages, the bisphosphonate is expected to have a sustained inhibitory activity on the monocytes/macrophages. This sustained activity is sufficient to modulate the monocyte/macrophage's inflammatory action. Thus, prolonged release of the agent is not required in order to sustain inhibition. Accordingly, the method of treating certain diseases by inhibiting monocytes/macrophages, such as, for example, by the use of an encapsulated agent, is preferably a systemic therapy, in that the formulation targets both the circulating monocytes and the tissue-resident macrophages. Depending on the specific bisphosphonate in the formulation, the phagocytic monocytes and macrophages may respond differently. For example, alendronate-encapsulated liposomes may cause apoptosis, while clodronate-encapsulated liposomes may cause necrosis.

The formulation for use in the methods of the invention may be provided in a variety of pharmaceutical forms for administration, depending on the various factors specific for each patient (e.g., the severity and type of disorder, age, body weight, response, and the past medical history of the patient), the number and type of therapeutic agents in the formulation, the type of formulation (e.g., encapsulated, embedded, particulate, etc.), the form of the composition (e.g., in liquid, semi-liquid or solid form), and/or the route of administration (e.g., oral, intravenous, intramuscular, intra-arterial, intramedullary, intrathecal, intraventricular, transdermal, subcutaneous, intraperitoneal, intranasal, enteral, topical, sublingual, vaginal, or rectal means). Pharmaceutical carriers, vehicles, excipients, or diluents may be included in the compositions of the invention including, but not limited to, water, saline solutions, buffered saline solutions, oils (e.g., petroleum, animal, vegetable or synthetic oils), starch, glucose, lactose, sucrose, gelatin, malt, rice, flour, chalk, silica gel, sodium stearate, glycerol monostearate, talc, sodium chloride, dried skim milk, glycerol, propylene, glycol, ethanol, dextrose and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Formulations suitable for parenteral administration may be prepared in aqueous solutions, preferably in physiologically compatible buffers such as Hanks' solution, Ringer's solution, or physiologically buffered saline. Aqueous injection suspensions may contain substances, which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

The bisphosphonate may be provided in any form, for example, including salts, salt solvates, and hydrates thereof. Thus, for example, when encapsulated, the bisphosphonate may be a solid or in solution, and the solid may be a solvate or a hydrate.

Administration of the Formulation

The present invention is meant to encompass administering the formulation containing an effective amount of one or more bisphosphonates in a regimen of one or more doses to treat or manage HIV/AIDS. The number of doses used will be as may be necessary to achieve the desired effect, for example, 1, 3, 5, 8 or 10, once a day, b.i.d., q.i.d., or continuously as a continual infusion over a period of time.

The formulation of the current invention may be administered in combination with other medicaments. The term "in combination" is not limited to the administration of the medicaments at exactly the same time, but rather it is meant that the formulation of the invention and other medicament are administered to a patient in a sequence and within a time interval such that they can act together to provide an increased benefit than if they were administered otherwise. For example, the formulation of the invention and other medicament may be administered at the same time or sequentially in any order at different points in time; however, if not administered at the same time, they should be administered sufficiently close in time so as to provide the desired therapeutic effect. Each administration of the formulation of the current invention, whether or not in combination with other medicaments, can be conducted separately, in any appropriate form and by any suitable route which effectively transports the therapeutic agent to the appropriate or desirable site of action. Preferred modes of administration of the formulation of the invention include intravenous (i.v.) and intra-arterial (i.a.). Other suitable modes of administration include intramuscular (i.m.), subcutaneous (s.c.), and intraperitonal (i.p.) and oral (per os). Such administration may be bolus injections or infusions. Another mode of administration may be by perivascular delivery. Combinations of any of the above routes of administration may also be used in accordance with the invention.

When administered, it is desirable that the formulation is administered at a dose and at a time that the monocyte/macrophage inhibiting effect lasts the entirety of the ensuing TI. In one embodiment, the formulation is administered at least once during a period shortly before TI, for example, from about 3 to about 10 days before the end of the antiviral therapy. In another embodiment, the formulation may be administered multiple times during the antiviral therapy. In yet another embodiment, the formulation may be administered during TI, either in addition to the pre-TI administration or without administration during the immediately preceding antiviral therapy. Since the management of HIV/AIDS is a long-term endeavor and may include multiple antiviral therapies juxtaposed by TI, it is therefore in accordance with the invention to encompass multiple rounds of the monocyte/macrophage-inhibiting treatments in accordance with the invention at appropriate time points in conjunction with the antiviral therapy regime and TI.

The term "effective amount" denotes an amount of the bisphosphonate in the formulation which is effective in inhibiting or decreasing the activity of monocytes/macrophages to prolong reemergence of active virions and/or effective in eliminating or reducing the number of circulating monocytes/macrophages. An effective amount of the bisphosphonate in the formulation is contemplated to provide long-term treatment to complement antiviral therapy in the management of HIV/AIDS. It is preferable that the effective amount of bisphosphonate in the formulation inhibits and/or depletes monocytes/macrophages for a period that is about one week, about two weeks, preferably ≥one month, more preferably ≥two months, still more preferably ≥three months, most preferably up to or longer than six months. The skilled artisan could determine the period of effectiveness empirically by administering the formulation to an individual in need thereof (or an animal model of such an individual) and monitoring the level of inhibition/depletion at different time points. One may also correlate the time of inhibition with the appropriate desired clinical effect, e.g., inhibition of HIV viral loads and/or increase in the level of $CD4^+$ T cells.

The effective amount of bisphosphonate in the formulation may depend on several factors including, but not limited to: gender, age and weight of the patient; the mode of administration of the formulation; the type of carrier used to encapsulate or embed bisphosphonate (e.g., whether it is a carrier that rapidly releases bisphosphonate or a carrier that releases it over a period of time); the treatment regimen (e.g., whether the formulation is administered once every few days, once every few weeks, or once per antiviral therapy); the status of the HIV/AIDS, including the strain of the virus, the viral loads and $CD4^+$ T cell counts of the treated individual before and after the administration of the formulation.; the types and amounts of the drugs used in the antiviral cocktail; drug resistance of the patient; genotype of the patient as it relates to HIV/AIDS susceptibility; duration of the antiviral therapy; duration of the TI. A skilled artisan, by routine experimentation, can determine the effective amount based on the above factors or other relevant factors, and the description herein.

Exemplary, non-limiting, doses of bisphosphonate for the formulation of the invention for use in humans are contemplated to be, for example, between about 1.5 ng/kg to about 10 mg/kg body weight, or between about 15 ng/kg to about 15 micrograms/kg body weight, or between about 0.15 mg/kg to about 15 micrograms/kg body weight, or between about 0.15 mg/kg to about 1.5 mg/kg body weight micrograms/kg body weight. Thus, for example, a patient might receive a dose in the range of about 0.1 microgram to about 1 mg, e.g., about 0.1 microgram, or about 1 microgram, or about 10 micrograms, or about 100 micrograms, or about 1 mg. Other doses may also be used, depending on the particular bisphosphonate used, the particular formulation and the dosage regimen, as can be readily determined by the skilled artisan.

Data obtained from cell culture assays and animal studies can be used to determine a dosage range of the formulation for use in humans. The dose of bisphosphonate in the formulation preferably results in a range of circulating concentration that includes the $ED_{50}$ with little or no toxicity. The dosage for a particular patient will depend upon the particular formulation employed, the route of administration utilized, and condition or characteristics of the patient. For any formulation used in the method of the invention, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. The effective doses in humans may be further determined via clinical trials.

Characterization of Therapeutic Utility

In one embodiment, the desired therapeutic result of inhibiting or decreasing monocyte/macrophage activity and/or eliminating or reducing the number of monocytes/macrophages is the suppression of HIV viral loads and/or the increase of $CD4^+$ T cells for a sufficient period of time. A sufficient period of time may be the entirety of a TI. In certain cases, a sufficient period may be longer or shorter than the entirety of a TI.

Toxicity and efficacy of the therapeutic methods of the instant invention can be determined by standard pharmaceutical procedures in cell cultures or experimental animals, e.g., for determining the $LD_{50}$ (the dose lethal to 50% of the population), the No Observable Adverse Effect Level (NO-AEL) and the $ED_{50}$ (the dose therapeutically effective in 50% of the population). The dose ratio between toxic and therapeutic effects is the therapeutic index and it can be expressed as the ratio $LD_{50}/ED_{50}$ or $NOAEL/ED_{50}$. Formulations that exhibit large therapeutic indices are preferred. While formulations that exhibit toxic side effects may be used, care should be taken to design a delivery system that targets the agents of such formulations to the site of target cells in order to minimize potential damage to unaffected cells and, thereby, reduce side effects. In addition, drug carriers of such formulations should be designed to control the drug release so that the level of released drug does not exceed any toxicity limit.

The protocols and compositions of the inventive method are preferably tested in vitro, and then in vivo, for the desired therapeutic activity, prior to use in humans. One example, of such an in vitro assay is an in vitro cell culture assay in monocytes and/or macrophages which are grown in culture, and exposed to or otherwise administered to cells, and observed for an effect of this assay upon the cells, e.g., inhibited or decreased activity and/or complete or partial cell death. The monocytes/macrophages may be obtained from an established cell line or recently isolated from an individual as a primary cell line. Many assays standard in the art can be used to measure the activity of the formulation on the monocytes/macrophages, for example, by quantitating the levels of chemotactic factors such as macrophage chemoattractant protein-1 (MCP-1), interleukin 1 beta (IL-1B), tissue necrosis factor alpha (TNF-α) and macrophage inflammatory protein-1 alpha (MIP-1 alpha). Many assays standard in the art can be used to assess survival and/or growth of the monocytes/macrophages; for example, cell proliferation can be assayed by measuring $^3H$-thymidine incorporation, by direct cell count, by detecting changes in transcriptional activity of known genes such as proto-oncogenes (e.g., fos, myc) or cell cycle markers; cell viability can be assessed by trypan blue straining.

The contents of all published articles, books, reference manuals and abstracts cited herein, are hereby incorporated by reference in their entirety to more fully describe the state of the art to which the invention pertains.

EXAMPLES

The following examples as set forth herein are meant to illustrate and exemplify the various aspects of carrying out the present invention and are not intended to limit the invention in any way.

Liposomal alendronate (LA) may be prepared, for example, in accordance with the protocols described in Epstein-Barash, H., et al., J. CONTROLLED RELEASE, 146:182-195 (2010); Epstein, H. et al., AAPS J, 10:505-515 (2008); and U.S. patent application Ser. No. 13/804,707. More particularly, for the purposes of Examples 2-7, LA was prepared in accordance with U.S. patent application Ser. No. 13/804,707, reproduced herein as Example 1.

Example 1—Liposomal Alendrondate Preparation

A one liter batch of liposomal alendronate encapsulated in liposomes containing cholesterol, DSPC and DSPG, and dispersed in phosphate buffer saline solution was produced. Liposomal alendronate may be provided in two concentrations, for clinical convenience: 5 mg/ml and 0.5 mg/ml, as a sterile whitish, liposomal dispersion. These concentrations may be further formulated to obtain a desired amount of therapeutic agent in any specific volume. The lipid ingredients were composed of cholesterol, DSPC and DSPG. The dispersion also contained a phosphate buffer saline solution for pH control, infusion suitability and for the maintenance of isotonicity. At least 96% of the drug in the final product was encapsulated in the liposomes. For administration, the content of the vial (or part of it, as needed) was diluted with a saline vehicle, and then administered as an infusion. In one specific pre-clinical Example, the appropriate mass of LA (determined by body weight) was diluted in room temperature 1×PBS to a final volume of 20 ml and administered at 4 ml/minute by intravenous (saphenous vein) or intraperitoneal injection.

A batch formula that includes the amount and quality of the components used in the manufacturing process and their amounts on a per 1 liter batch basis is presented in Table 1 below.

TABLE 1

Liposomal Alendronate for IV Infusion, Batch Formula for 1 Liter

| Component | Amount | Quality |
|---|---|---|
| Alendronate Sodium trihydrate | 68-80.75 g | 100.5% |
| NaOH | 6.8-8.0 g | Extra pure |
| Cholesterol | 10 ± 0.2 g | ≥99% |
| DSPC | 30 ± 0.4 g | ≥99% |
| DSPG | 10 ± 0.2 g | ≥99% |
| Ethanol | 77 ± 1.1 ml | Absolute, extra pure |
| t-butanol | 77 ± 1.1 ml | For analysis |
| Water for injection | 850 ± 13 ml | USP |
|  | 6 ± 0.1 ml |  |
| PBS pH 7 | ~6000 ml |  |
| $Na_2HPO_4 \cdot 2H_2O$ | 13.86 g ± 1.5% | Extra pure |
| $NaH_2PO_4 \cdot 2H_2O$ | 6.54 g ± 1.5% | Extra pure |
| NaCl | 50.82 g ± 1.5% | Extra pure |
| Water For Injection | 6000 ml | USP |

The contents and quantitative composition of liposomal alendronate for IV infusion produced in the 1 liter batch of Table 1 are summarized in Table 2 below. It is noted that in this batch, the molar ratio of DSPC:DSPG:cholesterol was 3:1:2. Also, the drug:lipid ratio was calculated to be about 1:5.7±1.5 w:w.

TABLE 2

Composition of Liposomal Alendronate for IV Infusion

| | Component | Composition 0.5 mg/ml | Composition 5 mg/ml |
|---|---|---|---|
| Drug substance | Sodium Alendronate trihydrate | 0.5 ± 0.05 mg/ml = 0.0015 mmol/ml | 5.0 ± 0.2 mg/ml = 0.015 mmol/ml |
| Liposomal lipids | Cholesterol | 0.6 ± 0.1 mg/ml = 0.0015 mmol/ml | 5.2 ± 0.8 mg/ml = 0.013 mmol/ml |
| | DSPC (1,2-Distearoyl-sn-glycero-3-phosphocholine) | 1.7 ± 0.3 mg/ml = 0.0022 mmol/ml | 15.65 ± 2.35 mg/ml = 0.020 mmol/ml |
| | DSPG (1,2-Distearoyl-sn-glycero-3-phospho-rac-glycerol) | 0.6 ± 0.1 mg/ml = 0.0007 mmol/ml | 5.2 ± 0.8 mg/ml = 0.006 mmol/ml |
| Buffer solution (pH 7) | $NaH_2PO_4 \cdot 2H_2O$ | 1.09 mg/ml | 1.09 mg/ml |
| | $Na_2HPO_4 \cdot 2H_2O$ | 2.31 mg/ml | 2.31 mg/ml |
| | NaCl | 8.47 mg/ml | 8.47 mg/ml |
| | Water for injection (WFI) | ~1 ml | ~1 ml |

A liposomal alendronate formulation for IV infusion actually produced by the manufacturing process described herein is presented in Table 3 below.

TABLE 3

Specifications for 5 mg/ml Dosage Form

| Tests | Specification |
|---|---|
| Appearance | Whitish dispersion |
| Identification | Conforms |
| Alendronate Assay (HPLC) | 5.0 ± 0.2 mg/mL |
| Alendronate Encapsulation | ≥96% |
| DSPC Assay (HPLC) | 13.3-18.0 mg/mL |
| DSPG Assay (HPLC) | 4.4-6.0 mg/mL |
| Cholesterol Assay (HPLC) | 4.4-6.0 mg/mL |
| Drug:Lipid ratio (w:w) including Cholesterol | 1:5.3 ± 1.0 |
| Vesicle Size | Mean particle diameter 80 ± 5 nm |
| pH | 6.7-7.3 |
| Ethanol | <0.5% |
| t-Butanol | <0.5% |
| Osmolality | 270-340 osmol/kg |
| Sterility | Sterile |
| Pyrogens | Pass |

A 0.5 mg/ml dosage strength may be manufactured by the same process as the 5 mg/ml dosage strength, described above. Only the final standardization step (described below) differs in forming a different final formulation concentration for administration. A concentration of 0.5 mg/ml was used for the Examples below. The skilled person in the art understands that other dosages may be manufactured pursuant to this process.

The therapeutic agent solution (alendronate solution) and lipid solution were prepared as follows:

Alendronate Solution.

NaOH (6.8-8.0 g) was weighed and dissolved in 850 ml water for injection (WFI), with temperature at 70±3° C., 600±150 RPM. Complete dissolution was verified by visual inspection. Sodium Alendronate (68 to 80.75 g) was dissolved in the NaOH solution, with temperature at 70±3° C., stirring at 600±150 RPM. Complete dissolution was verified by visual inspection (i.e., clear solution), conductivity and pH measurements were verified (pH=6.8±0.3. Conductivity=18.0±1 ms/cm).

Lipid Solution.

Lipids comprising 30 g DSPC (37.9 mmoles), 10 g DSPG (12.5 mmoles), and 10 g cholesterol (25.8 mmoles) (DSPC/DSPG/Cholesterol; 3/1/2 mol/mol/mol) were weighed and dissolved in a 250 ml beaker on a heated magnetic stirrer in 160 ml of t-butanol/EtOH/$H_2O$ (77/77/6, v/v/v) at temperature of 70±3° C., forming a lipid solution with a concentration of 312 mg/ml. A clear yellow solution was formed once the temperature was within limits.

MLV Formulation.

The lipid solution was added to the alendronate solution (1 part drug; 5.3 parts lipid) while mixing at 600+150 RPM and maintaining temperature 70±3° C. After at least 5 minutes, 100 ml WFI (10% of total volume) was added to reduce solvent concentration before extrusion. The formulation was mixed for additional 10 minutes.

Extrusion.

The formulation was subjected to extrusion by 1.2 L heated stainless steel extruder assembled with one 0.14 μm ceramic membrane or with two polycarbonate membranes (e.g., a 0.2 pre-filter and 0.1 μm membrane) to reduce the size of the vesicles and improve the vesicle homogeneity at pressure=90±15 psi and temperature=68±5° C. The process required 12-18 passes to achieve vesicles of 80-100 nm. Extrusion passes were sampled in real time to verify vesicle size before ultrafiltration. The liposome formulation size was analyzed using Malvern Nano ZS analyzer (acceptance limits: 95±20 nm). An extrusion sample was also analyzed for aerobic bacterial count (bio-burden control). The acceptance limit was <100 CFU/ml.

Ultrafiltration and Diafiltration.

First, the formulation was allowed to cool to <45° C. before undergoing ultrafiltration. Ultrafiltration was performed on Amersham QuixStand system with a 500K hollow fiber membrane. The formulation was concentrated using an inlet pressure not exceeding 25 psi. Upon reaching a minimal volume, the formulation was dialyzed with 10 initial volumes (~7 L) of a phosphate buffer saline (PBS) solution. The PBS solution was prepared by dissolving 145 mM NaCl, 13 mM $Na_2HPO_4$, and 7 mM $NaH_2PO_4$ in 10 L WFI. The PBS had pH about 6.9 and conductivity about 16.9 ms/cm. The PBS was filtered through a 0.2 μm filter. Diafiltration end was marked by measuring the pH and conductivity of the dialyzed formulation The formulation was drained from the ultrafiltration system not exceeding 120% of initial volume (~1.2 liter). A sample was taken for general analysis and for aerobic bacterial count (bio-burden control). The acceptance limit was <1,000 CFU/ml.

At the end of dialysis, the formulation was filtered through 0.2 μm filter to maintain bio-burden control. A pressure vessel containing the formulation was connected to a sterile 0.2 μm filter (Sartorius Sartobran P). The filter was pre-assembled to a sterile reception tank. Filtration is performed by applying pressure of 5-30 psi on the pressure vessel. A sample was taken for general analysis and for aerobic bacterial count (bio-burden control). The acceptance limit was <100 CFU/ml.

Final Standardization.

The formulation was analyzed for size, lipid/therapeutic agent composition in the liposome, drug and free therapeutic agent content by HPLC. The expected yield in this example was a one liter formulation containing about 6 mg/ml encapsulated alendronate and 35 mg/ml lipids. Based on the results of the alendronate concentration, the required dilution was calculated to achieve about one liter of final formulation concentration of 5 mg/ml or 0.5 mg/ml. To produce the 5 mg/ml formulation, about 900 ml liposomal alendronate after ultrafiltration were diluted with about 100 ml PBS, prepared as described above. Additionally, to produce the 0.5 mg/ml formulation, about 100 ml liposomal alendronate after ultrafiltration were diluted with about 900 ml PBS for 0.5 mg/ml concentration. A sample was taken to determine the achieved concentration of alendronate.

Following the production of the standard formulation concentration, a bottle containing the formulation was connected to two sequential sterile 0.2 μm filters (Sartorius Sartobran P) located in a class 100 room or a sterile biological hood. The filter was pre-assembled to a pre-sterilized disposable reception bag or bottle. Filtration was performed by a peristaltic pump or pressurized nitrogen. Pressure should not exceed 10 psi. When filtration was ended the filter was tested for integrity.

The liposome alendronate for IV infusion produced in the above example had a number of desirable properties, for example (i) three year stability of at least the alendronate and lipids at 5° (range 2-8° C.); (ii) average vesicle diameter of 80±5 with no particulate matter; (iii) a concentration of alendronate sodium of up to 5 mg/ml (range 0.1-5.0 mg/ml); (iv) alendronate encapsulation greater than or equal to 96%; (v) lipid composition of distearoyl phosphatidylcholine/distearoyl phosphatidylglycerol/cholesterol (DSPC/DSPG/CHOL) of 3/1/2 mol/mol/mol; (vi) physiological osmolality of 270-340 mO/kg, (vii) viscosity similar to water, i.e., dynamic viscosity of about 1.0 mPa s at 20° C.; (viii) pH 6.8 (range 6.8-7.0); (ix) worldwide acceptability of excipient quality in accordance with the US or EP Pharmacopeia; (x) meets USP guidelines for sterility and pyrogens as published in the USP 24-NF 19; (xi) compatibility (use) with saline, infusion kits and syringes; and (xii) compatibility (process) with filters, tubing stainless steel and glass.

Example 2

Liposomal Alendronate Depleted Monocytes in Nonhuman Primates.

The ability of LA to deplete monocytes was tested in cynomolgus macaques. Specifically, two cynomolgus macaques were treated with a single 0.1 mg/kg i.v. dose of LA (LA 1 and LA 2). The absolute and relative frequencies of CD14+ monocytes in whole blood were then assessed through 7 days post injection (d.p.i.) by flow cytometry. The results are presented in FIGS. 1A-1B. Cynomolgus macaques receiving 0.1 mg/kg of LA i.v. showed a ~50% reduction in CD14+ monocyte frequency by 1 d.p.i. As shown in FIGS. 1A-1B, this depletion was transient, however, as CD14+ monocyte frequencies returned to baseline levels by 2 d.p.i. Thus, LA was shown to be effective for monocyte depletion in nonhuman primates.

Blood Processing.

Whole blood was collected into EDTA treated tubes (BD Biosciences, San Jose, Calif.). A 500 μl aliquot was used to assess complete blood counts (CBC) using a Horiba/ABX Pentra 60C+ (Horiba, Irvine, Calif.).

Flow Cytometric Analysis of Monocytes/Macrophages.

An 11-color flow cytometric staining panel was designed and optimized for the analysis of monocytes/macrophages in the blood and tissues of rhesus macaques, as set forth in Table 4.

TABLE 4

Monocyte/macrophage staining panel designed for flow cytometry.

| Antibody | Clone | Fluorophore | Manufacturer | Location |
|---|---|---|---|---|
| MAC387 | MAC387 | FITC | AbCam | Intracellular |
| CD163 | GHI/61 | PE | Biolegend | Surface |
| CD68 | KP1 | PerCP-Cy5.5 | Santa Cruz Biotechnology | Intracellular |
| CD45 | D058-1283 | APC | BD Biosciences | Surface |
| CD3 | SP34-2 | Pacific Blue | BD Biosciences | Surface |
| HLA-DR | G46-6 | Alexa Fluor 700 | BD Biosciences | Surface |
| CD14 | RMO52 | ECD | Beckman Coulter | Surface |
| CD8 | B9.11 | PE-Cy5 | Beckman Coulter | Surface |
| CD16 | 3G8 | PE-Cy5 | BD Biosciences | Surface |
| CD20 | 2H7 | APC-H7 | BD Biosciences | Surface |
| ARD | — | Live/Dead Yellow | Invitrogen | — |

Either 100 μl whole blood or 1×10⁶ total tissue cells were washed twice in 1×PBS and then surface stained for 30 minutes at room temperature. Whole blood and spleen were then incubated in 1 ml FACSLyse for 10 minutes, spun at 830×g for 4 minutes, and washed three times in 1×PBS supplemented with 10% fetal calf serum (FACS buffer). Other tissue cells were washed once in 1×PBS and fixed in 2% paraformaldehyde. For intracellular stains, fixed cells were washed twice in FACS buffer containing 1 mg/ml saponin (saponin buffer) and stained for 1 hour at room temperature. For intranuclear stains (BrdU and Ki-67), fixed cells were washed twice in a 1:1 mixture of saponin buffer and 2×BD FACSPerm, then washed once in saponin buffer and stained for 1 hour at room temperature in the presence of 0.5 mg/ml DNase I. Following staining, samples were washed twice in saponin buffer and then run on a BD-LSRII (Becton Dickinson, Franklin Lakes, N.J.). Flow cytometric data was analyzed using FlowJo version 9.6.4 (TreeStar, Ashland, Oreg.). All positive gates were set by using fluorescence minus one (FMO) control tubes for the appropriate fluorophore.

Example 3

Liposomal Alendronate is Well-Tolerated in Nonhuman Primates.

The safety of LA treatment was examined in the nonhuman primate model. Serum concentrations of four key readouts of liver function (albumin, alanine transaminase, alkaline phosphatase, and bilirubin) were monitored in four rhesus macaques, each receiving one of two different LA-treatment regimens. FIGS. 2A-2D illustrate serum chemistry analysis of rhesus macaques receiving a repeated low-dose (0.1 mg/kg i.v. each day for one week; Rh22618 and Rh28450) or a single high-dose (10 mg/kg i.v.; Rh28438 and Rh29054) of LA. Dotted lines represent the expected ranges of albumin, alanine transaminase, alkaline phosphatase, and total bilirubin serum concentrations based on rhesus macaque population statistics at the Oregon National Primate Research Center. Serum chemistry of the animals receiving the repeated low dose injections of LA was sampled on days 0, 3 and 7. Serum chemistry of the animals receiving the single high-dose injection of LA was followed for two days prior to necropsy.

Figures 2A, 2B:
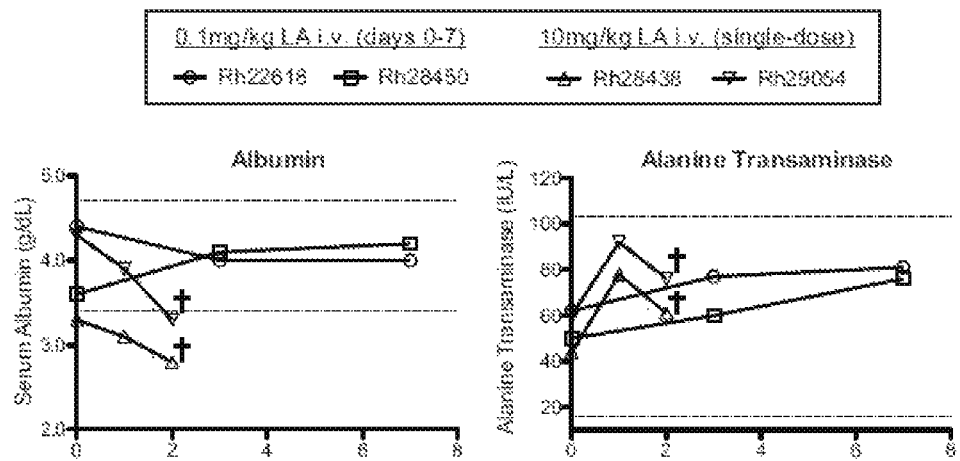
FIGS. 2A-2D illustrate serum chemistry in rhesus macaques at various times after different dose regimens of liposomal alendronate.
Figures 2C, 2D:
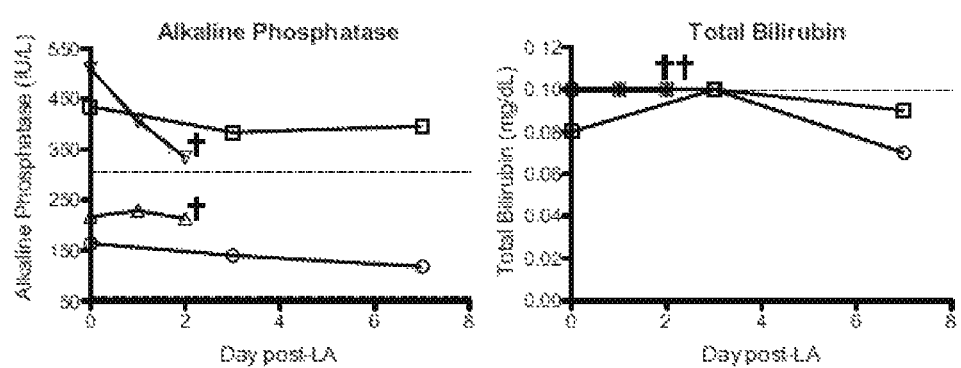

As illustrated in FIGS. 2A-2D, repeated low-dose LA administration revealed no change in liver function, while a single high-dose led to perturbation of liver function. Specifically, a comparison between baseline measurements and post-LA measurements revealed no adverse changes in serum chemistry in animals receiving repeated low dose LA (Rh22618 and Rh28450). All values fell within expected ranges with the exception of alkaline phosphatase in Rh28450, which was high at baseline (FIG. 2C). In contrast to the animals receiving daily low doses of LA, the animals receiving the single high dose of LA (Rh28438 and Rh29054) exhibited decreased serum concentrations of albumin (FIG. 2A), coincident with elevated concentrations of alanine transaminase (FIG. 2B), although alanine transaminase concentrations were within expected values. These changes in albumin and alanine transaminase serum concentrations are indicative of liver exertion, likely due to the depletion of liver Kupffer cells (see below). Despite these findings, no adverse clinical side effects of LA treatment were observed in the high dose animals, nor in any animals receiving LA, regardless of dose or frequency. It is important to note that 0.1 mg/kg of LA i.v. was sufficient to deplete monocytes (FIGS. 1A-1B), and this dose of LA was safe in rhesus macaques, even upon repeated daily injections (FIGS. 2A-2D). Therefore, LA is well tolerated at effective doses and constitutes a viable new technique for monocyte depletion in nonhuman primates.

Rhesus macaques were housed at the Oregon National Primate Research Center. The Oregon Health & Science University Institutional Animal Care and Use Committee reviewed and approved all study protocols, which were in accordance with the U.S. Department of Health and Human Services Guide for the Care and Use of Laboratory Animals.

Example 4

LA Treatment at an Alternative Dose and Route Produces Monocyte Depletion in Another Nonhuman Primate Model.

Figure 3A:
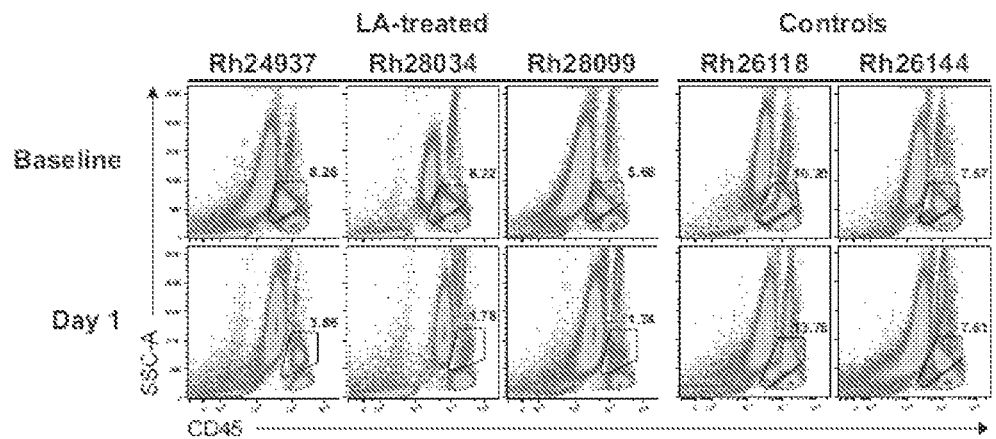
FIGS. 3A-3B illustrate the effect of administering a single 1 mg/kg dose of liposomal alendronate, compared to vehicle control, on monocyte frequency (FIG. 3A) and monocyte subset frequency (FIG. 3B) in rhesus macaques, measured using a flow cytometry staining panel.
Figure 3B:
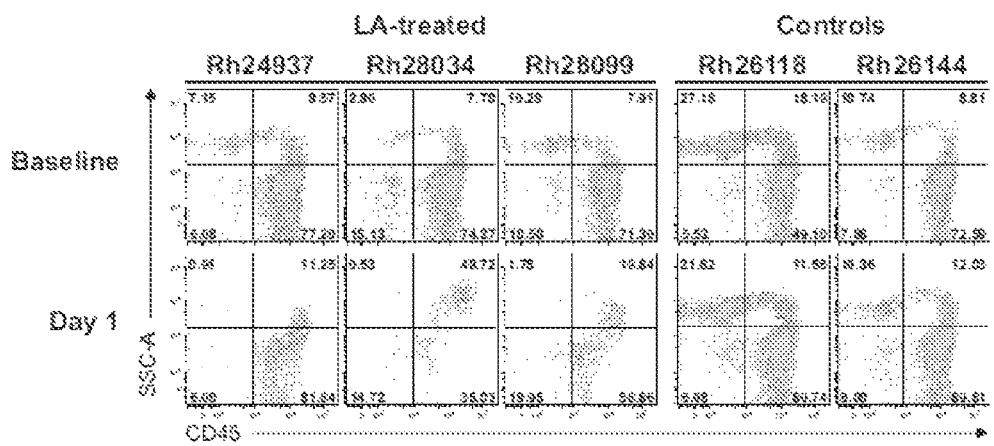

A different dose and route of LA administration was observed to produce a greater monocyte depletion in rhesus macaques compared to controls, as illustrated in FIGS. 3A-3B. Three rhesus macaques (Rh24937, Rh28034, and Rh28099) were injected with 1 mg/kg of LA both i.v. and intraperitoneally (i.p.) and monitored the frequency of monocytes at 1 d.p.i. using the flow cytometry staining panel described above. Two control rhesus macaques (Rh26118 and Rh26144) received phosphate-buffered saline injections with the same volumes and routes as the LA-treated animals. The monocyte population was distinguishable from lymphocytes and granulocytes by distinct CD45 mean fluorescence intensities (MFI) versus side scatter profiles (FIG. 3A).

FIG. 3A illustrates the frequency of monocytes, one day after a single 1 mg/kg dose of LA to rhesus macaques compared to control, measured using the flow cytometry staining panel set forth in Table 4. Specifically, FIG. 3A illustrates the frequency of monocytes in whole blood pre- and post-LA treatment, determined by flow cytometric analysis of CD45 MFI versus side scatter profile. Following LA treatment, large decreases in monocyte frequency were observed at 1 d.p.i., with a particularly pronounced depletion in Rh28034 (baseline: 8.22%; 1 d.p.i.: 1.78%). In contrast, monocyte frequencies in the control animals remained stable at 1 d.p.i. (FIG. 3A).

To further assess the monocyte depletion observed in the LA-treated rhesus macaques, subsets of monocytes were evaluated to determine which were most affected. The frequency of three previously described monocyte subsets (classical CD14+CD16−, intermediate CD14+CD16+, and non-classical CD14−CD16+) [24] were compared within the total monocyte pool, before and after LA treatment. The results are illustrated in FIG. 3B. Specifically, FIG. 3B illustrates the frequency of monocyte subsets, one day after a single 1 mg/kg dose of LA to rhesus macaques compared to control, measured using the flow cytometry staining panel set forth in Table 4. Specifically, FIG. 3B illustrates the frequency of monocyte subsets in whole blood pre- and post-LA treatment, determined by flow cytometric analysis of CD14+ versus CD16+ staining Significant animal-to-animal variability was observed when comparing monocyte subset frequencies pre- and post-treatment. Importantly, LA-treated rhesus macaques exhibited depletion of nearly all CD14−CD16+ monocytes at 1 d.p.i., while the control rhesus macaques maintained similar monocyte subset frequencies at 1 d.p.i., supporting the observed lack of overall monocyte depletion (FIGS. 3A-3B).

Figures 4A, 4B, 4C, 4D:
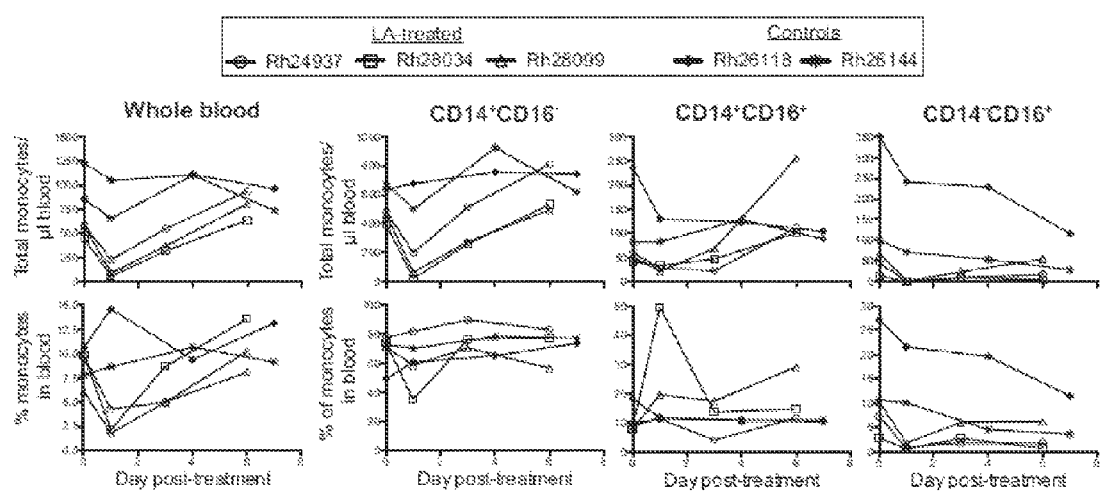
FIGS. 4A-4D illustrate the effect of administering a single 1 mg/kg dose of liposomal alendronate, compared to vehicle control, on absolute counts and frequencies of monocytes and three monocyte subsets in whole blood of rhesus macaques over 7 days.

To determine the duration of the depletion, the absolute counts and frequencies of monocytes were monitored through 7 d.p.i. The results are illustrated in FIGS. 4A-4D, in which the open symbols represent the LA-treated animals and the closed symbols represent the control animals. The top row of FIGS. 4A-4D illustrates the absolute monocyte counts in whole blood pre- and post-LA treatment. Absolute monocyte counts were calculated by assessing the frequency of CD14+ and/or CD16+ monocytes and comparing this value to the overall white blood cell count (CD45+ cells). The bottom row of FIGS. 4A-4D illustrates the frequency of monocytes in whole blood pre- and post-LA treatment assessed by flow cytometry. Consistent with the data showing large decreases in monocyte frequency following LA treatment, the absolute counts of monocytes per microliter of blood also showed substantial declines at 1 d.p.i. (FIG. 4A, bottom). This was most pronounced in Rh28034 and Rh28099, where absolute monocyte counts decreased 87% and 84%, respectively. Interestingly, absolute monocyte counts also revealed the preservation of CD14+CD16+ monocytes following LA treatment. This was in sharp contrast to the large declines in monocyte counts observed in the CD14+CD16− and CD14-CD16+ populations (FIGS. 4A-4D, top row). The monocyte depletion observed in these LA-treated rhesus macaques was highly transient, similar to that observed in cynomolgus macaques treated with a single 0.1 mg/kg dose of LA i.v. (FIGS. 1A-1B; FIGS. 4A-4D, bottom row). Therefore, LA treatment can safely induce significant, but highly transient, depletion of monocytes in rhesus macaques.

Example 5

LA Treatment Reduces the Frequency of Tissue-Resident Macrophages and Increases the Frequency of Bone Marrow Monocytes.

As shown above, liposomal alendronate consistently depletes tissue-resident macrophages and induces bone marrow monocyte generation in the non-human primate model. To determine whether the consistent monocyte depletion in nonhuman primate cohorts observed after LA administration (FIGS. 1A-1B; FIGS. 4A-4D) is paralleled by a decrease in the frequency of tissue-resident macrophages and bone marrow monocytes, various tissues were collected and macrophage/monocyte frequencies were assessed using the 11 color flow cytometric staining panel (Example 2, Table 4) using a gating procedure. Bronchoalveolar lavages (BAL), colon biopsies, liver biopsies, and bone marrow aspirates were collected before and after LA treatment from six rhesus macaques by the tissue processing method described below. FIGS. 5A-5E illustrate a gating strategy for the identification of macrophages in the tissues (defined as MAC387+ and/or CD163+) and bone marrow (defined as CD163+), as represented for colon tissue.

Figures 6A, 6B, 6C:
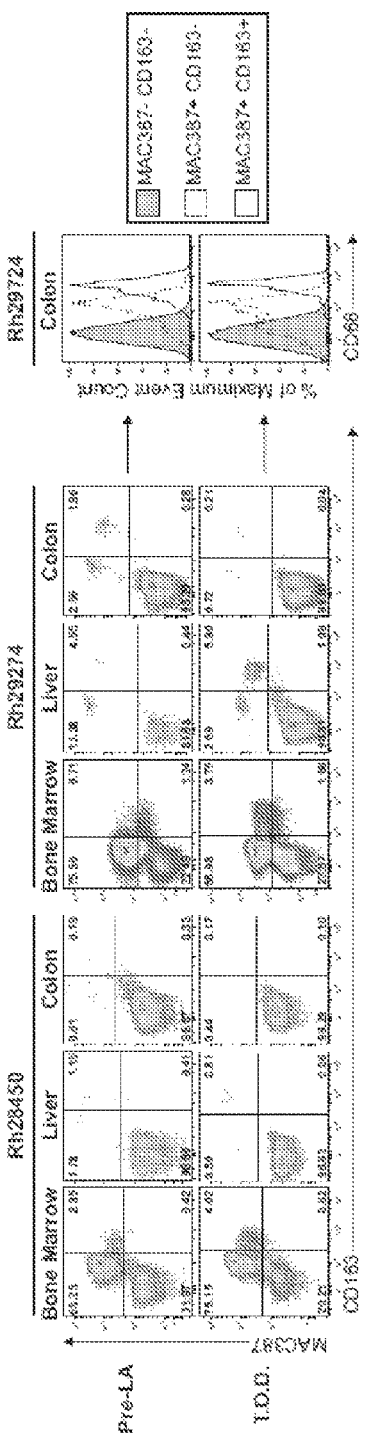
FIGS. 6A-6C illustrate representative tissue resident macrophage and bone marrow myeloid precursor staining from various tissues in rhesus macaques.

No change in the frequency of alveolar macrophages was observed in the BAL following LA treatment (data not shown). FIGS. 6A-6C illustrate representative tissue resident macrophage and bone marrow myeloid precursor staining from Rh28450 and Rh29724. More particularly, FIGS. 6A-6C (FIG. 4B) show comparative examples of MAC387 versus CD163 staining before and after LA treatment from bone marrow aspirate, liver and colon. MAC387 is an antibody that recognizes the calcium-binding myeloid-related protein MRP14, which is expressed in tissue-resident macrophages [25-27]. This staining panel identified three distinct macrophage populations in these tissues: MAC387+ CD163−, MAC387+CD163+, and MAC387−CD163+. In general, as shown in FIGS. 6A-6B, MAC387−CD163+ macrophages were found at a lower frequency than the MAC387+CD163− and MAC387+CD163+ macrophages. To further evaluate these three populations of tissue macrophages, their expression of CD68, a glycoprotein also expressed in tissue-resident macrophages [26, 28, 29], was examined. Specifically CD68 expression in the MAC387+ CD163− and MAC387+CD163+ populations from the colon of Rh29724 before and after LA treatment was compared to that of MAC387-CD163+(shaded). FIG. 6C illustrates that CD68 expression of the three populations from the colon of Rh29724 before and after LA treatment had similar staining profiles at both time points. FIG. 6C also shows that MAC387+CD163− and MAC387+CD163+ macrophages both expressed CD68, with the latter population showing the highest expression, confirming that our flow cytometric panel was able to identify tissue macrophages. Thus, the depletion of tissue-resident macrophages following LA treatment of nonhuman primates using three previously described macrophage markers is shown herein, for the first time.

Figures 7A, 7B, 7C:
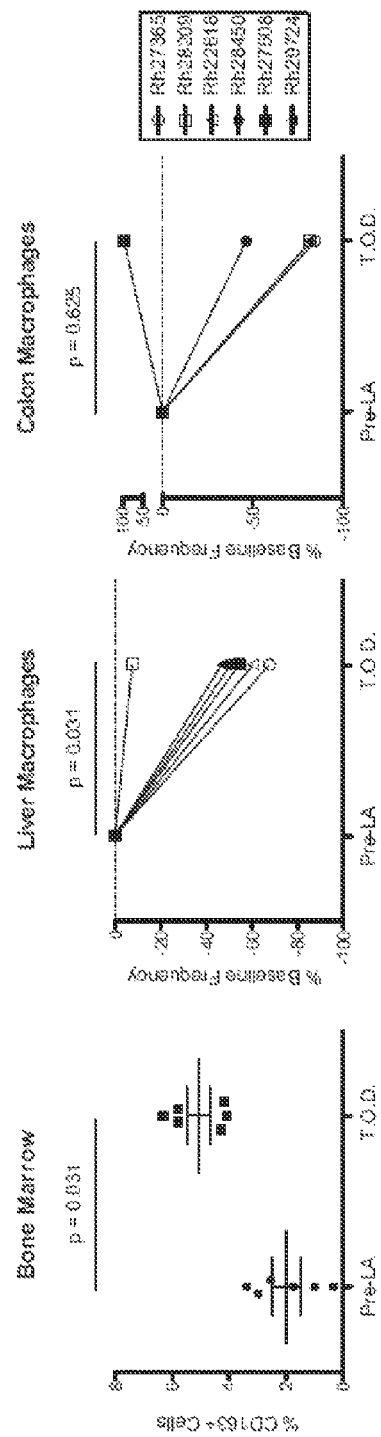
FIGS. 7A-7C illustrate the frequency of macrophages and myeloid precursors in tissue and bone marrow of rhesus macaques before and after liposomal alendronate treatment.

The analysis was extended to determine the effectiveness of LA treatment on monocyte depletion in the bone marrow. Because blood monocytes express both MAC387 and CD163 following emigration from the bone marrow, the frequency of cells expressing these markers in the bone marrow was examined before and after LA treatment in six rhesus macaques. In a similar fashion, tissue macrophage depletion was assessed in the liver and colon. FIG. 7A depicts the frequency of CD163+ cells in the bone marrow before and after LA treatment. FIG. 7B depicts tissue-resident macrophage frequency (percent change from baseline) in liver before and after LA treatment. FIG. 7C depicts the frequency of tissue-resident macrophages in colon before and after LA treatment.

Staining of bone marrow aspirates revealed little change in the overall frequency of monocytes when defined as MAC387+ and/or CD163+(data not shown). However, given that granulocytes in the bone marrow may also express MAC387, a separate analysis was performed to define bone marrow monocytes as CD163+[25]. A significant increase in monocyte precursor production in the bone marrow was observed, as illustrated in FIG. 7A. Specifically, this analysis revealed significant increases in bone marrow monocyte frequency following the administration of LA (p=0.031) (FIG. 7A). Despite an initial hypothesis that LA treatment would deplete bone marrow monocytes, this finding is not altogether surprising, as SIV-associated depletion of tissue macrophages has been shown to increase myeloid turnover, beginning with monocyte release from the bone marrow [30]. However, the possibility that monocyte depletion occurs in the bone marrow prior to the earliest time point examined (1 d.p.i.) cannot be dismissed.

As illustrated in FIGS. 7B-7C, tissue-resident macrophage frequencies were decreased by LA treatment. FIG. 7B reveals a significant decrease in the liver. FIG. 7C shows that four of five rhesus macaques had decreases in colon macrophages, although this was not significant due to a single animal exhibiting an increase in colon macrophage frequency. Specifically, macrophage frequencies in the liver were reduced by >45% following LA treatment in five of the six animals studied (p=0.031; FIG. 4D, left panel). Significance tests for FIGS. 7A-7C were all Wilcoxon signed-rank. Given that Kupffer cells constitute 80-90% of tissue macrophages in the human body, this result highlights the effectiveness of LA in tissue macrophage depletion [31]. It is important to note that the majority of depleted macrophages in the liver were MAC387+CD163− (FIG. 7B, and data not shown). This same trend was observed in the colon, where overall macrophage frequency was reduced by >45% in four of five animals (Rh22618 excluded from analysis due to undetectable macrophage frequency pre-LA)(p=0.625). In the colon, however, the depletion was more evenly distributed across the three macrophage populations (FIG. 7C, and data not shown). Surprisingly, one of the animals (Rh27508) showed a large increase in macrophage frequency in the colon. However, this animal also exhibited the above described expansion of CD163+ monocytes in the bone marrow, a >80% reduction in absolute monocyte count, and a >50% reduction in macrophage frequency in the liver, providing ample evidence of a direct effect of LA treatment (FIGS. 7B-7C). Therefore, one cannot exclude the possibility that the increase in colon macrophage frequency is a result of differential myeloid cell turnover kinetics following LA-associated depletion in this animal.

Tissue Processing.

Bronchoalveolar lavages were filtered through 70 µm strainers. Bone marrow was pelleted by centrifugation at 830×g for 4 minutes, then resuspended and vigorously shaken in 1×PBS containing 2 mM EDTA to disassociate large cell clumps. Cells were washed twice in RPMI-1640 containing 10% fetal calf serum (R10) (Hyclone Laboratories, Logan, Utah). Lymph nodes and spleen were diced with scalpels and then mashed through a 70 µm cell strainer. The strainer was rinsed repeatedly with R10 to obtain a single cell suspension. Colon and liver were diced into 5 mm³ pieces and approximately 25-30 of these pieces were placed in a 50 ml conical containing 25 ml RPMI-1640 supplemented with 3% fetal calf serum (R3). Dithiothreitol was added at a final concentration of 200 µM and tissues were shaken at 225 rpm for 15 minutes at room temperature. Tissues were allowed to settle and the R3 with DTT was aspirated and replaced with R3 containing 5 mM EDTA. Tissues were shaken at 225 rpm for 30 minutes at 37° C. and the cell containing supernatant was collected and passed through a cell strainer. R3 containing EDTA was again added, tissues shaken, and cells collected. Tissues were washed twice in 1× Hank's balanced salt solution to remove excess EDTA and then were suspended in R3 containing 0.1 mg/ml collagenase (Sigma-Aldrich, St. Louis, Mo.) and 0.1 mg/ml DNase I (Roche, Indianapolis, Ind.). Tissues were shaken at 225 rpm for 45 minutes at 37° C. and the cell containing supernatant was collected and passed through a 70 µm cell strainer. R3 containing collagenase and DNase I was again added, tissues shaken, and cells collected. Cell fractions collected from the EDTA and collagenase digestion steps were combined (total tissue) and resuspended in 30% isotonic percoll (GE Healthcare, Buckinghamshire, UK). The cells were then layered over a 60%/40% percoll gradient and spun at 500×g with the brake off. Mononuclear cells from the lower interface were collected and washed in R10.

Example 6

5'-Bromo-2'-Deoxyuridine (BrdU) Reveals Monocyte Turnover Following LA Treatment.

As illustrated by the data above, monocytes were consistently detected following LA treatment, but the data does not differentiate whether the monocytes were newly emigrated cells from the bone marrow or simply remainders from the original cellular pool. The increased frequencies of $CD163^+$ bone marrow monocytes suggested that blood monocyte turnover is exacerbated following LA treatment. To provide a more detailed characterization of monocyte turnover, support the depletion results, and allow for a better calculation of total blood monocyte depletion, LA treatments were designed and executed, in tandem with BrdU administration, to ascertain the level of monocyte turnover in this nonhuman primate model.

BrdU is a synthetic thymidine analogue that is incorporated into the DNA of dividing cells during S phase and can be detected by intracellular antibody staining [32, 33]. Dividing monocyte precursors in the bone marrow integrate BrdU before being released into the blood as monocytes. Following release from the bone marrow, monocytes and tissue-resident macrophages rarely divide, making BrdU a reliable marker of myeloid cell turnover [30].

To assess monocyte turnover, two rhesus macaques, Rh28438 and Rh29054, received 10 mg/kg of LA i.v., along with 60 mg/kg of BrdU i.v. Control animal Rh31577 received phosphate-buffered saline along with the same 60 mg/kg dose of BrdU. BrdU was suspended at 10 mg/ml in HBSS (Hank's balanced salt solution) (HyClone Laboratories, Logan, Utah). BrdU 60 mg/kg was injected intravenously (saphenous vein) at a rate of 2-3 ml/minute. FIGS. 8A-8C reveal both monocyte depletion and high monocyte turnover following LA treatment. LA treatment depleted the majority of blood monocytes based on: frequency assessed by CD45 staining versus side scatter profile (FIG. 8A) and absolute monocyte counts (FIG. 8B). BrdU staining (FIG. 8C) revealed high levels of monocyte turnover following LA treatment in both the $CD14^+CD16^-$ (classical) and $CD14^+CD16^-$ (intermediate) monocyte populations. Values shown indicate percent of total $CD14^+CD16^-$ (classical) and $CD14^+CD16^+$ (intermediate) populations staining positive for BrdU. To determine the level of monocyte turnover following LA treatment, two rhesus macaques (Rh28438 and Rh29054) were injected with 10 mg/kg of LA i.v., along with 60 mg/kg of BrdU i.v., and monitored the frequency of $BrdU^+$ and $BrdU^-$ monocytes through 2 d.p.i. Control animal Rh31577 received phosphate-buffered saline along with the same 60 mg/kg dose of BrdU. As illustrated in FIG. 8A, LA treatment in Rh28438 and Rh29054 again led to a profound decrease in the frequency of monocytes by 1 d.p.i. Unexpectedly, control animal Rh31577 also exhibited a decline in monocyte frequency, albeit to a smaller extent.

To confirm that Rh31577 was indeed an appropriate control, in view of the observed decrease in monocyte frequency in this animal (FIG. 8A), absolute monocyte counts were assessed before and after LA-treatment in all three rhesus macaques. As expected, large decreases in monocyte counts were observed in the LA-treated animals, while monocyte counts in Rh31577 remained unchanged following phosphate-buffered saline injection, as illustrated in FIG. 8B.

Finally, the emigration of monocytes from the bone marrow ($BrdU^+$) was monitored by comparing LA-treated animals to the control (FIG. 8C). Interestingly, a higher frequency of $CD14^+CD16^-BrdU^+$ monocytes in LA-treated animals was observed compared to the control animal at 1 d.p.i., with more than half of $CD14^+CD16^-$ monocytes staining positive for BrdU in Rh28438 (FIG. 8C, left panel). FIG. 8C also shows that ≥10% of $CD14^+CD16^+$ monocytes stained positive for BrdU in LA-treated animals at 1 d.p.i., in sharp contrast to control animal Rh31577, which had no $CD14^+CD16^+BrdU^+$ monocytes at 1 d.p.i. Acute inflammation leads to increased monocyte turnover, as monocytes enter the affected tissues to differentiate into macrophages [34]. In the case of rhesus macaques infected with simian immunodeficiency virus (SIV), monocyte turnover is a strong predictor of progression to AIDS [30]. Similarly, high levels of monocyte turnover correlate to the severity of SIV-induced encephalitis in rhesus macaques [35]. Remarkably, the levels of monocyte turnover we observed in LA-treated animals at 1 d.p.i. were similar or greater to those seen in SIV-infected rhesus macaques, including rapid progressors with severe encephalitis [30, 35]. Thus, LA treatment increases blood monocyte turnover, a finding in support of the increased bone marrow monocyte generation and blood monocyte depletion data. Additionally, these levels of blood monocyte turnover are comparable to advanced SIV infection, where marked turnover of monocytes is observed.

Summary of the Effects of LA on Monocytes and Macrophages

Thus it is shown for the first time that LA is a safe and effective means of monocyte and tissue macrophage depletion in the nonhuman primate model. Importantly, a selective monocyte subset depletion is demonstrated here for the first time, with $CD14^+CD16^-$ and $CD14^-CD16^+$ monocytes exhibiting strong depletion compared to the CD14$^+$CD16$^+$ subset. Administration of LA consistently reduced absolute monocyte counts and tissue macrophage frequencies in the liver and colon. This depletion was associated with a significant increase in monocyte generation in the bone marrow, a finding supported by increased monocyte turnover in the blood as measured by DNA BrdU incorporation.

LA-mediated monocyte depletion was highly transient in all nonhuman primates examined, and this finding is in full support of previous work with rabbits, rats, and humans, where LA depletion of monocytes is also transient. Importantly, transient monocyte depletion has been shown to trigger a profound and sustained anti-inflammatory effect, exemplified by the reduced incidence of restenosis and endometriosis following LA treatment [23, 36, 37]. Consequently, the usefulness of LA administration to nonhuman primates may extend well beyond the time frame of monocyte depletion.

In contrast to liver and colon, no depletion of alveolar macrophages were detected in the lung following LA treatment. The reason for this difference is unclear but, without being bound by theory, may depend on the biodistribution or macrophage targeting of LA in the lung. Given the large number of macrophages in the lung (~70% of lung immune cells), it is possible that the mass of LA reaching the lung following i.v. or i.p. injection is insufficient to deplete a detectable number of cells [38]. Additionally, systemic LA administration (i.v. and i.p.) may inhibit the depletion of alveolar macrophages at the mucosal surface of the lung, given that the small amounts of LA leaving the liver will be carried via blood. This LA would encounter, and potentially target, alternate lung tissue macrophages, such as interstitial macrophages.

Two major populations of macrophages were observed in the tissues of rhesus macaques: MAC387$^+$CD163$^+$ and MAC387$^+$CD163$^-$. However, in humans MAC387$^+$ macrophages have been characterized as M1-like and CD163$^+$ macrophages as M2-like, with little to no co-expression of these markers on the same cells. Supporting this identification of MAC387$^+$CD163$^+$ tissue macrophages, a recent study in rhesus macaques comprehensively characterized the markers expressed by different populations of lung-resident macrophages, showing that both blood monocytes and interstitial macrophages co-express high levels of MAC387 and CD163 [38]. Functional analysis of this cellular population revealed that MAC387$^+$CD163$^+$ interstitial macrophages respond to classical macrophage activation signals (IFNγ and LPS). Therefore, MAC387$^+$CD163$^+$ appears to define an M1-like population of macrophages, although anatomical location may affect expression of these markers, as MAC387$^+$CD163$^+$ macrophages are rare in rhesus macaque brain tissue [26].

The analyses conducted herein were aided by the design of an 11-color flow cytometric staining panel that was universally applied to blood and tissues for the identification of monocytes and macrophages, respectively. See Example 2, Table 4 above. Studies have relied heavily on macrophage cell lines such as U937 and in vitro monocyte-derived macrophages, which may not truly recapitulate the complexities of tissue-resident macrophages [42-44]. The evaluation of tissue-resident macrophages by flow cytometry provides the advantage of sorting live cells, a technique not afforded by traditional immunohistochemical and immunofluorescent staining techniques. Given the numerous roles of macrophages in physiological processes, the ability to perform functional assays on macrophages directly ex vivo has implications across multiple fields of study.

Nonhuman primates provide a powerful model of human biology. Here, the nonhuman primate model is advanced by showing, for the first time, that monocytes and macrophages can be experimentally depleted by administration of LA. Given the scientific insight gained by depletion of T cells, B cells, and NK cells in nonhuman primates [8-13], it is believed that the technique described herein further strengthens the nonhuman primate model and provides a unique avenue for the study of the many physiological processes of blood monocytes and tissue macrophages.

Example 7—HIV/AIDS Treatment Protocol

Figure 9:
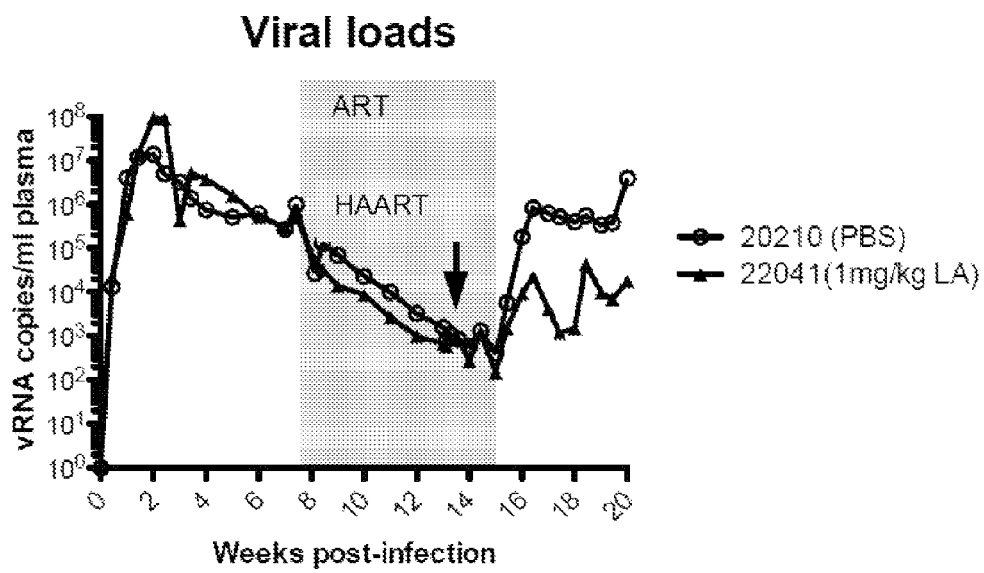
FIG. 9 illustrates the effect of administering a liposomal bisphosphonate, alendronate 1 mg/kg, compared to vehicle control, on the viral load of SHIV-infected rhesus macaques.
Figure 10:
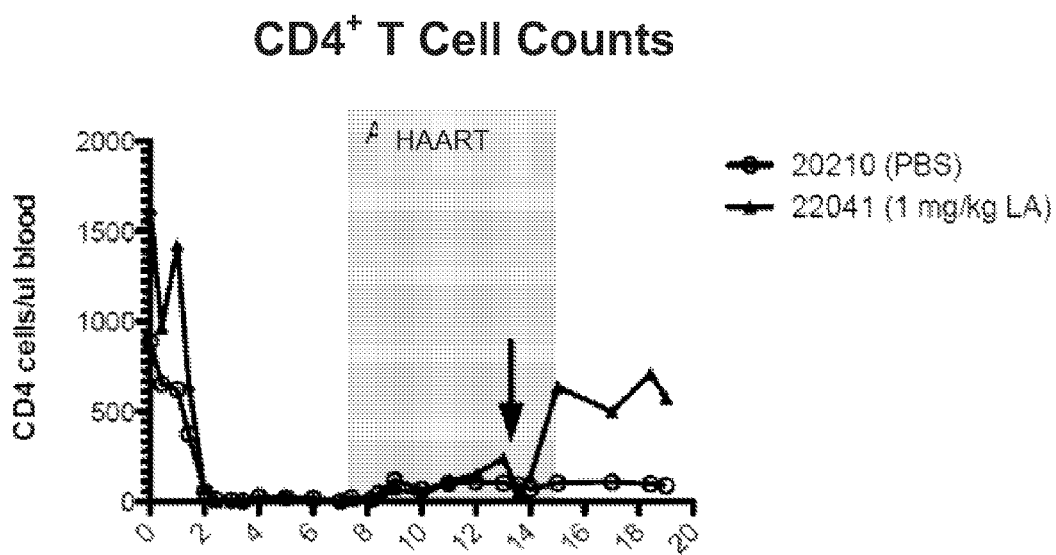
FIG. 10 illustrates the effect of administering 1 mg/kg liposomal alendronate, compared to vehicle control, on peripheral CD4+ counts in SHIV-infected rhesus macaques.

The effect of liposomal alendronate on the plasma viral loads and peripheral CD4$^+$ T cell counts following HAART cessation was evaluated in an animal model. Specifically, the ability of LA to decrease or deplete the HIV reservoirs was tested in an Indian rhesus macaque model of AIDS. Rhesus macaques have been extensively used in AIDS research, and the species is one of the best characterized non-human primate model for HIV/AIDS. (See Pereira, L. E. et al., Immunodeficiency, Ch. 15, available at http://dx.doi.org/10.5772/53556.) Two macaques were infected with a hybrid Simian Human Immunodeficiency Virus (SHIV) and plasma viral loads and peripheral CD4 T cell counts were followed longitudinally. The SHIV used in this study, SHIV DH12 clone 7, systemically depletes CD4$^+$ T cells and then begins to replicate in macrophages, similar to the late chronic stage of HIV infection in humans. As is shown in FIGS. 9 and 10, the animals received HAART to suppress viral replication starting from close to 8 weeks after SHIV infection, when the virus began to replicate in macrophages.

LA was prepared following the protocol described in Example 1.

To test the effect of a formulation according to the invention during HAART, one animal received LA in the dose of 1 mg/kg body weight administered intravenously, while the other animal as a control received an i.v. injection of phosphate buffered saline (PBS). Timing of this administration is represented by the arrow in FIGS. 9 and 10. Following this administration, HAART was continued for one and a half additional weeks until close to week 15 post-infection, to protect target cells during the cycling of the macrophage compartment due to LA-mediated depletion of these cells. Plasma viral loads and peripheral CD4$^+$ T cell counts of the two animals were monitored regularly from infection until about week 20 post-infection.

Plasma viral loads ("VL"), i.e., the amount of replicating HIV in the blood, were evaluated by measuring viral RNA copy numbers per mL of blood plasma. The measurement is a conventional assay in HIV/AIDS research and was performed following the protocol described in Friedrich, T. C. et al., "Subdominant CD8+ T-cell responses are involved in durable control of AIDS virus replication." J. VIROLOGY, 81(7):3465-76 (2007).

FIG. 9 illustrates the effect of intravenously injected LA on the VL of a SHIV-infected macaque, compared to a SHIV-infected macaque receiving placebo (i.v. PBS) control. VL is denoted as the viral RNA copies per mL of blood plasma. The shaded area represents the duration of the HAART therapy, and the arrow points to the time point when liposomal alendronate is administered. In particular, FIG. 9 illustrates the kinetics and magnitudes of viral loads over the course of the entire study. Both animals experienced an increase in replicating virus within the first week after HAART cessation, but the LA-treated animal exhibited a consistent 1-2 log reduction in plasma viral loads compared to the control animal until at least week 20 post-infection.

The number of peripheral $CD4^+$ T cells reflects the severity of HIV/AIDS, with a lower count corresponding to higher HIV replication and more damage to the immune system. Peripheral $CD4^+$ T cell counts may be measured in a conventional assay in HIV/AIDS research and in this example were measured following the protocol described in Friedrich, T. C. et al., "Subdominant CD8+ T-cell responses are involved in durable control of AIDS virus replication." J. VIROLOGY, 81(7):3465-76 (2007).

FIG. 10 illustrates the effect of intravenously injected LA on peripheral $CD4^+$ T cell counts of a SHIV-infected macaque, compared to a SHIV-infected macaque receiving placebo i.v. PBS (control). $CD4^+$ T cell counts are denoted in the number of $CD4^+$ T cells per micro-L of blood. The shaded area represents the duration of the HAART therapy, and the arrow points to the time point when liposomal alendronate is administered. In particular, FIG. 10 illustrates the change in $CD4^+$ T cell counts over the course of the entire study. The $CD4^+$ T cells in both animals decreased rapidly after SHIV infection and were nearly depleted after two weeks. Both animals had a limited increase in peripheral $CD4^+$ T cell counts after the beginning of the antiviral therapy. As is shown in FIG. 10, the LA-treated animal experienced a marked rebound in peripheral $CD4^+$ T cell counts after LA administration, and the rebound lasted at least about 5 weeks. The control animal, which was not treated with LA, maintained the minimal level of peripheral $CD4^+$ T cells throughout the study.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

REFERENCES

1. Pollard, J. W. (2009) Trophic macrophages in development and disease. Nat Rev Immunol 9, 259-270.
2. Schneemann, M., Schoeden, G. (2007) Macrophage biology and immunology: man is not a mouse. J Leukoc Biol 81, 579; discussion 580.
3. Murray, P. J., Wynn, T. A. (2011) Obstacles and opportunities for understanding macrophage polarization. J Leukoc Biol 89, 557-563.
4. Haigwood, N. L. (2009) Update on animal models for HIV research. Eur J Immunol 39, 1994-1999.
5. Yang, S. H., Cheng, P. H., Banta, H., Piotrowska-Nitsche, K., Yang, J. J., Cheng, E. C., Snyder, B., Larkin, K., Liu, J., Orkin, J., Fang, Z. H., Smith, Y., Bachevalier, J., Zola, S. M., Li, S. H., Li, X. J., Chan, A. W. (2008) Towards a transgenic model of Huntington's disease in a non-human primate. Nature 453, 921-924.
6. Sacha, J. B., Kim, I. J., Chen, L., Ullah, J. H., Goodwin, D. A., Simmons, H. A., Schenkman, D. I., von Pelchrzim, F., Gifford, R. J., Nimityongskul, F. A., Newman, L. P., Wildeboer, S., Lappin, P. B., Hammond, D., Castrovinci, P., Piaskowski, S. M., Reed, J. S., Beheler, K. A., Tharmanathan, T., Zhang, N., Muscat-King, S., Rieger, M., Fernandes, C., Rumpel, K., Gardner, J. P., Gebhard, D. H., Janies, J., Shoieb, A., Pierce, B. G., Trajkovic, D., Rakasz, E., Rong, S., McCluskie, M., Christy, C., Merson, J. R., Jones, R. B., Nixon, D. F., Ostrowski, M. A., Loudon, P. T., Pruimboom-Brees, I. M., Sheppard, N. C. (2012) Vaccination with Cancer- and HIV Infection-Associated Endogenous Retrotransposable Elements Is Safe and Immunogenic. J Immunol 189, 1467-1479.
7. Tachibana, M., Sparman, M., Sritanaudomchai, H., Ma, H., Clepper, L., Woodward, J., Li, Y., Ramsey, C., Kolotushkina, O., Mitalipov, S. (2009) Mitochondrial gene replacement in primate offspring and embryonic stem cells. Nature 461, 367-372.
8. Choi, E. I., Reimann, K. A., Letvin, N. L. (2008) In vivo natural killer cell depletion during primary simian immunodeficiency virus infection in rhesus monkeys. J Virol 82, 6758-6761.
9. Friedrich, T. C., Valentine, L. E., Yant, L. J., Rakasz, E. G., Piaskowski, S. M., Furlott, J. R., Weisgrau, K. L., Burwitz, B., May, G. E., Leon, E. J., Soma, T., Napoe, G., Capuano, S. V., Wilson, N. A., Watkins, D. I. (2007) Subdominant CD8+ T-cell responses are involved in durable control of AIDS virus replication. J Virol 81, 3465-3476.
10. Ortiz, A. M., Klatt, N. R., Li, B., Yi, Y., Tabb, B., Hao, X. P., Sternberg, L., Lawson, B., Carnathan, P. M., Cramer, E. M., Engram, J. C., Little, D. M., Ryzhova, E., Gonzalez-Scarano, F., Paiardini, M., Ansari, A. A., Ratcliffe, S., Else, J. G., Brenchley, J. M., Collman, R. G., Estes, J. D., Derdeyn, C. A., Silvestri, G. (2011) Depletion of CD4(+) T cells abrogates post-peak decline of viremia in SIV-infected rhesus macaques. J Clin Invest 121, 4433-4445.
11. Haberthur, K., Engelmann, F., Park, B., Barron, A., Legasse, A., Dewane, J., Fischer, M., Kerns, A., Brown, M., Messaoudi, I. (2011) CD4 T cell immunity is critical for the control of simian varicella virus infection in a nonhuman primate model of VZV infection. PLoS Pathog 7, e1002367.
12. Hansen, S. G., Powers, C. J., Richards, R., Ventura, A. B., Ford, J. C., Siess, D., Axthelm, M. K., Nelson, J. A., Jarvis, M. A., Picker, L. J., Fruh, K. (2010) Evasion of CD8+ T cells is critical for superinfection by cytomegalovirus. Science 328, 102-106.
13. Gordon, S. N., Cecchinato, V., Andresen, V., Heraud, J. M., Hryniewicz, A., Parks, R. W., Venzon, D., Chung, H. K., Karpova, T., McNally, J., Silvera, P., Reimann, K. A., Matsui, H., Kanehara, T., Shinmura, Y., Yokote, H., Franchini, G. (2011) Smallpox vaccine safety is dependent on T cells and not B cells. J Infect Dis 203, 1043-1053.
14. Van Rooijen, N., Sanders, A. (1994) Liposome mediated depletion of macrophages: mechanism of action, preparation of liposomes and applications. J Immunol Methods 174, 83-93.
15. Gutman, D., Golomb, G. (2012) Liposomal alendronate for the treatment of restenosis. J Control Release 161, 619-627.
16. van Rooijen, N., Hendrikx, E. (2010) Liposomes for specific depletion of macrophages from organs and tissues. Methods Mol Biol 605, 189-203.
17. Epstein-Barash, H., Gutman, D., Markovsky, E., Mishan-Eisenberg, G., Koroukhov, N., Szebeni, J., Golomb, G. (2010) Physicochemical parameters affecting liposomal bisphosphonates bioactivity for restenosis therapy: internalization, cell inhibition, activation of cytokines and complement, and mechanism of cell death. J Control Release 146, 182-195.
18. Epstein, H., Gutman, D., Cohen-Sela, E., Haber, E., Elmalak, O., Koroukhov, N., Danenberg, H. D., Golomb, G. (2008) Preparation of alendronate liposomes for enhanced stability and bioactivity: in vitro and in vivo characterization. AAPS J 10, 505-515.
19. Kim, W. K., Sun, Y., Do, H., Autissier, P., Halpern, E. F., Piatak, M. J., Lifson, J. D., Burdo, T. H., McGrath, M. S., Williams, K. (2010) Monocyte heterogeneity underlying phenotypic changes in monocytes according to SIV disease stage. J Leukoc Biol 87, 557-567.
21. Danenberg, H. D., Fishbein, I., Epstein, H., Waltenberger, J., Moerman, E., Monkkonen, J., Gao, J., Gathi, I., Reichi, R., Golomb, G. (2003) Systemic depletion of macrophages by liposomal bisphosphonates reduces neointimal formation following balloon-injury in the rat carotid artery. J Cardiovasc Pharmacol 42, 671-679.
22. van Beek, E. R., Cohen, L. H., Leroy, I. M., Ebetino, F. H., Lowik, C. W., Papapoulos, S. E. (2003) Differentiating the mechanisms of antiresorptive action of nitrogen containing bisphosphonates. Bone 33, 805-811.
23. Banai, S., Finkelstein, A., Almagor, Y., Assali, A., Hasin, Y., Rosenschein, U., Apruzzese, P., Lansky, A. J., Kume, T., Edelman, E. R. (2013) Targeted anti-inflammatory systemic therapy for restenosis: the Biorest Liposomal Alendronate with Stenting sTudy (BLAST)-a double blind, randomized clinical trial. Am Heart J 165, 234-40.e1.
24. Ziegler-Heitbrock, L., Ancuta, P., Crowe, S., Dalod, M., Grau, V., Hart, D. N., Leenen, P. J., Liu, Y. J., MacPherson, G., Randolph, G. J., Scherberich, J., Schmitz, J., Shortman, K., Sozzani, S., Strobl, H., Zembala, M., Austyn, J. M., Lutz, M. B. (2010) Nomenclature of monocytes and dendritic cells in blood. Blood 116, e74-e80.
25. Goebeler, M., Roth, J., Teigelkamp, S., Sorg, C. (1994) The monoclonal antibody MAC387 detects an epitope on the calcium-binding protein MRP14. J Leukoc Biol 55, 259-261.
26. Soulas, C., Conerly, C., Kim, W. K., Burdo, T. H., Alvarez, X., Lackner, A. A., Williams, K. C. (2011) Recently infiltrating MAC387(+) monocytes/macrophages a third macrophage population involved in SIV and HIV encephalitic lesion formation. Am J Pathol 178, 2121-2135.
27. Williams, D. W., Eugenin, E. A., Calderon, T. M., Berman, J. W. (2012) Monocyte maturation, HIV susceptibility, and transmigration across the blood brain barrier are critical in HIV neuropathogenesis. J Leukoc Biol 91, 401-415.
28. Mansfield, K., Lang, S. M., Gauduin, M. C., Sanford, H. B., Lifson, J. D., Johnson, R. P., Desrosiers, R. C. (2008) Vaccine protection by live, attenuated simian immunodeficiency virus in the absence of high-titer antibody responses and high-frequency cellular immune responses measurable in the periphery. J Virol 82, 4135-4148.
29. Rogler, G., Hausmann, M., Vogl, D., Aschenbrenner, E., Andus, T., Falk, W., Andreesen, R., Scholmerich, J., Gross, V. (1998) Isolation and phenotypic characterization of colonic macrophages. Clin Exp Immunol 112, 205-215.
30. Hasegawa, A., Liu, H., Ling, B., Borda, J. T., Alvarez, X., Sugimoto, C., Vinet-Oliphant, H., Kim, W. K., Williams, K. C., Ribeiro, R. M., Lackner, A. A., Veazey, R. S., Kuroda, M. J. (2009) The level of monocyte turnover predicts disease progression in the macaque model of AIDS. Blood 114, 2917-2925.
31. Bilzer, M., Roggel, F., Gerbes, A. L. (2006) Role of Kupffer cells in host defense and liver disease. Liver Int 26, 1175-1186.
32. Bischoff, R., Holtzer, H. (1970) Inhibition of myoblast fusion after one round of DNA synthesis in 5-bromodeoxyuridine. J Cell Biol 44, 134-150.
33. Gunduz, N. (1985) The use of FITC-conjugated monoclonal antibodies for determination of S-phase cells with fluorescence microscopy. Cytometry 6, 597-601.
34. Van Furth, R., Diesselhoff-den Dulk, M. C., Mattie, H. (1973) Quantitative study on the production and kinetics of mononuclear phagocytes during an acute inflammatory reaction. J Exp Med 138, 1314-1330.
35. Burdo, T. H., Soulas, C., Orzechowski, K., Button, J., Krishnan, A., Sugimoto, C., Alvarez, X., Kuroda, M. J., Williams, K. C. (2010) Increased monocyte turnover from bone marrow correlates with severity of SIV encephalitis and CD163 levels in plasma. PLoS Pathog 6, e1000842.
36. Danenberg, H. D., Golomb, G., Groothuis, A., Gao, J., Epstein, H., Swaminathan, R. V., Seifert, P., Edelman, E. R. (2003) Liposomal alendronate inhibits systemic innate immunity and reduces in-stent neointimal hyperplasia in rabbits. Circulation 108, 2798-2804.
37. Haber, E., Afergan, E., Epstein, H., Gutman, D., Koroukhov, N., Ben-David, M., Schachter, M., Golomb, G. (2010) Route of administration-dependent anti-inflammatory effect of liposomal alendronate. J Control Release 148, 226-233.
38. Cai, Y., Sugimoto, C., Arainga, M., Alvarez, X., Didier, E. S., Kuroda, M. J. (2014) In vivo characterization of alveolar and interstitial lung macrophages in rhesus macaques: implications for understanding lung disease in humans. J Immunol 192, 2821-2829.
39. Harker, J. A., Yamaguchi, Y., Culley, F. J., Tregoning, J. S., Openshaw, P. J. (2014) Delayed sequelae of neonatal respiratory syncytial virus infection are dependent on cells of the innate immune system. J Virol 88, 604-611.
40. Hartwig, S. M., Holman, K. M., Varga, S. M. (2014) Depletion of Alveolar Macrophages Ameliorates Virus-Induced Disease following a Pulmonary Coronavirus Infection. PLoS One 9, e90720.
41. Zaynagetdinov, R., Sherrill, T. P., Kendall, P. L., Segal, B. H., Weller, K. P., Tighe, R. M., Blackwell, T. S. (2013) Identification of myeloid cell subsets in murine lungs using flow cytometry. Am J Respir Cell Mol Biol 49, 180-189.
42. Berger, G., Durand, S., Fargier, G., Nguyen, X. N., Cordeil, S., Bouaziz, S., Muriaux, D., Darlix, J. L., Cimarelli, A. (2011) APOBEC3A Is a Specific Inhibitor of the Early Phases of HIV-1 Infection in Myeloid Cells. PLoS Pathog 7, e1002221.
43. Sacha, J. B., Giraldo-Vela, J. P., Buechler, M. B., Martins, M. A., Maness, N. J., Chung, C., Wallace, L. T., Leon, E. J., Friedrich, T. C., Wilson, N. A., Hiraoka, A., Watkins, D. I. (2009) Gag- and Nef-specific CD4+ T cells recognize and inhibit SIV replication in infected macrophages early after infection. Proc Natl Acad Sci USA 106, 9791-9796.
44. Song, E., Lee, S. K., Dykxhoorn, D. M., Novina, C., Zhang, D., Crawford, K., Cerny, J., Sharp, P. A., Lieberman, J., Manjunath, N., Shankar, P. (2003) Sustained small interfering RNA-mediated human immunodeficiency virus type 1 inhibition in primary macrophages. J Virol 77, 7174-7181.

What is claimed is:

1. A method of treating HIV/AIDS comprising administering to an individual in need thereof a formulation containing an effective amount of a bisphosphonate in a formulation having a particle size diameter in the range of about 0.03-1.0 microns.

2. The method of claim 1, wherein said bisphosphonate is encapsulated in said formulation particle.

3. The method of claim 2, wherein said encapsulating formulation particle is a liposome.

4. The method of claim 1, wherein said bisphosphonate is embedded in said formulation particle.

5. The method of claim 4, wherein said embedding formulation particle is selected from the group consisting of microparticles, nanoparticles, microspheres, and nanospheres.

6. The method of claim 1, wherein said formulation particle is bisphosphonate in particulate form.

7. The method of claim 6, wherein said particulate form is selected from the group consisting of aggregates, flocculates, colloids, polymer chains, insoluble salts and insoluble complexes.

8. The method of claim 1, wherein said bisphosphonate comprises a compound having formula (I):

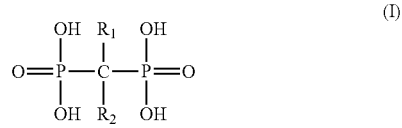

(I)

wherein $R_1$ is H, OH or halogen group; and $R_2$ is halogen; linear or branched $C_1$-$C_{10}$ alkyl or $C_2$-$C_{10}$ alkenyl, optionally substituted by heteroaryl or heterocyclyl $C_1$-$C_{10}$ alkylamino or $C_3$-$C_8$ cycloalkylamino; —NHY where Y is hydrogen, $C_3$-$C_8$ cycloalkyl, aryl or heteroaryl; or —SZ, where Z is chlorosubstituted phenyl or pyridinyl.

9. The method of claim 1, wherein said bisphosphonate is selected from the group consisting of clodronate, etidronate, tiludronate, pamidronate, alendronate and risendronate.

10. The method of claim 1, wherein said bisphosphonate is a nitrogenous bisphosphonate.

11. The method of claim 10, wherein said bisphosphonate is alendronate.

12. The method of claim 1, wherein said formulation particle has a diameter of about 0.07-0.15 microns.

13. The method of claim 1, wherein said bisphosphonate formulation is administered during an antiviral therapy.

14. The method of claim 13, wherein said bisphosphonate formulation is administered within a short period before an interruption of an antiviral therapy, said short period selected from the group consisting of: 3 days, 5 days, 7 days and 10 days.

15. The method of claim 1, wherein said bisphosphonate formulation is administered during an interruption of an antiviral therapy.

16. The method of claim 1, where said bisphosphonate formulation is administered both during an antiviral therapy and during an interruption of an antiviral therapy.

17. The method of claim 14, wherein the antiviral therapy is a highly active antiretroviral therapy (HAART).

18. The method of claim 1, wherein the administration is selected from the group consisting of: intravenous, intraarterial, intramuscular, subcutaneous or oral.

19. The method of claim 1, wherein the formulation further comprises a non-bisphosphonate therapeutic agent.

* * * * *